US007468272B2

(12) United States Patent
Chandrapati et al.

(10) Patent No.: US 7,468,272 B2
(45) Date of Patent: *Dec. 23, 2008

(54) BIOLOGICAL SOIL DETECTOR

(75) Inventors: Sailaja Chandrapati, Woodbury, MN (US); Bernard A. Gonzalez, St. Paul, MN (US); Bonnie J. Hovde, Woodbury, MN (US); Kevin D. Landgrebe, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 120 days.

This patent is subject to a terminal disclaimer.

(21) Appl. No.: 10/967,394

(22) Filed: Oct. 18, 2004

(65) Prior Publication Data
US 2005/0250089 A1 Nov. 10, 2005

Related U.S. Application Data

(63) Continuation-in-part of application No. 10/842,599, filed on May 10, 2004.

(51) Int. Cl.
*C12N 1/34* (2006.01)
(52) U.S. Cl. ................... 435/287.4; 435/288.5; 210/206
(58) Field of Classification Search .............. 435/287.4, 435/174, 288.5; 210/206
See application file for complete search history.

(56) References Cited

U.S. PATENT DOCUMENTS

| 3,616,251 | A |   | 10/1971 | Lecco et al. |
| 4,038,485 | A | * | 7/1977  | Johnston et al. ................. 435/4 |
| 4,301,115 | A | * | 11/1981 | Rapkin et al. .................. 422/56 |
| 4,702,840 | A |   | 10/1987 | Degen et al. |
| 5,004,543 | A |   | 4/1991  | Pluskal et al. |
| 5,096,833 | A |   | 3/1992  | Lau et al. |
| 5,128,041 | A |   | 7/1992  | Degen et al. |
| 5,132,208 | A |   | 7/1992  | Freitag et al. |
| 5,340,741 | A |   | 8/1994  | Lemonnier |
| 5,368,029 | A |   | 11/1994 | Holcombe et al. |
| 5,443,987 | A |   | 8/1995  | DeCicco et al. |
| 5,486,459 | A |   | 1/1996  | Burnham et al. |
| 5,552,272 | A |   | 9/1996  | Bogart |
| 5,827,675 | A |   | 10/1998 | Skiffington et al. |
| 5,928,948 | A |   | 7/1999  | Malchesky |
| 6,107,097 | A |   | 8/2000  | Pfeifer |
| 6,197,599 | B1|   | 3/2001  | Chin et al. |
| 6,203,496 | B1|   | 3/2001  | Gael et al. |
| 6,251,618 | B1|   | 6/2001  | Sugiyama et al. |
| 6,268,162 | B1| * | 7/2001  | Phillips et al. ................. 435/14 |
| 6,394,111 | B1|   | 5/2002  | Jacobs et al. |
| 6,428,746 | B1|   | 8/2002  | Muscarella et al. |
| 6,447,990 | B1|   | 9/2002  | Alfa |
| 6,454,874 | B1|   | 9/2002  | Jacobs et al. |
| 6,494,964 | B1|   | 12/2002 | Jacobs et al. |
| 6,506,818 | B1|   | 1/2003  | Choi et al. |
| 6,516,817 | B2|   | 2/2003  | Jacobs et al. |
| 6,551,834 | B2|   | 4/2003  | Carpenter et al. |
| 6,596,532 | B1|   | 7/2003  | Hyman et al. |
| 6,867,052 | B2|   | 3/2005  | Lander et al. |
| 7,193,519 | B2| * | 3/2007  | Root et al. ................ 340/573.1 |
| 2003/0012688 | A1 | | 1/2003 | Kippenhan |
| 2003/0064417 | A1 | | 4/2003 | Buechler et al. |
| 2003/0164182 | A1 | | 9/2003 | Jacobs et al. |
| 2004/0052679 | A1 | | 3/2004 | Root et al. |
| 2004/0142327 | A1 | | 7/2004 | Lin |
| 2005/0084842 | A1 | | 4/2005 | O'Connor |

FOREIGN PATENT DOCUMENTS

| AU | 199739216 | 4/1998 |
| EP | 0 269 979 | 6/1988 |
| EP | 0 884 115 | 12/1998 |
| EP | 1 213 583 | 12/2002 |
| JP | 3435234 | 4/1991 |
| JP | 10-313894 | 7/1999 |
| JP | 2002 355297 | 12/2002 |
| JP | 383599 | 8/2003 |
| WO | WO 00/10476 | 3/2000 |

(Continued)

OTHER PUBLICATIONS

D. Verjat et al., "Fluorescence-assay on Traces of Protein on Reusable Medical Devices: Cleaning Efficiency"; International Journal of Pharmaceutics; vol. 179, No. 2, Mar. 15, 1999, pp. 267-271.

(Continued)

*Primary Examiner*—Ralph Gitomer
(74) *Attorney, Agent, or Firm*—Dean A Ersfeld

(57) ABSTRACT

A biological soil detector and a method for detecting bio soil are provided. The biological soil detector has a solid support member; a specific indicator immobilized on the solid support member, the specific indicator having a material sensitive to the presence of blood; and the solid support and specific indicator positioned within or on a retaining member to readily contact a liquid that has been used to contact a surface. In the method for detecting bio soil, the method includes the following steps: contacting the surface with a liquid; after the liquid has contacted the surface, contacting the liquid with the solid support member and the specific indicator of the detector described herein; and inspecting the solid support member for a detectable response to determine whether the specific indicator has interacted with biological soil.

25 Claims, 8 Drawing Sheets

FOREIGN PATENT DOCUMENTS

| WO | WO 00/45943    | 8/2000  |
|----|----------------|---------|
| WO | WO 01/13109 A2 | 2/2001  |
| WO | WO 01/03663    | 5/2001  |
| WO | WO 01/54552    | 8/2001  |
| WO | WO 01/70641    | 9/2001  |
| WO | WO 01/89654    | 11/2001 |
| WO | WO 00/09743    | 2/2002  |
| WO | WO 03/063693   | 8/2003  |

OTHER PUBLICATIONS

Alfa Michelle J. et al.; "Worst-Case Soiling Levels for Patient-Used Flexible Endoscopes Before and After Cleaning"; *American Journal of Infection Control*, vol. 27, No. 5, Oct. 1999, pp. 392-401.

Klueh U. et al.; "Binding and Orientation of Fibronectin to Silanated Glass Surfaces Using Immobilized Bacterial Adhesin-Related Peptides" *Biomaterial*; Oct. 2003, pp. 3877-3884.

Costa S. A. et al., "Immobilisation of Catalase on the Surface of Biodegradable Starch-Based Polymers as a Way to Chance its Surface Characteristics" *Journal of Materials Science: Materials in Medicine*; Apr. 2004; pp. 335-342.

Barer M. R.; "New Possibilities for Bacterial Cytochemistry: Light Microscopical Demonstration of Beta-Galactosidase in Unfixed Immobilized Bacteria" *The Histochemical Journal*; Nov.-Dec. 1991, vol. 23, No. 11-12, Nov. 1991 pp. 529-533.

Ishino Y et al.; "Pitfalls in Endoscope Reprocessing: Brushing of Air and Water Channels is Mandatory for High-Level Disinfection"; *Gastrointestinal Endoscopy*, Feb. 2001, vol. 53, No. 2, Feb. 2001, pp. 165-168.

Van Pouke S.O. et al., "Rapid Detection of Fluorescent and Chemiluminescent Total Coliforms and *E. coli* on Membrane Filters" *Journal of Microbiological Methods*, vol. 42, pp. 233-244, 2000.

\* cited by examiner

US 7,468,272 B2

BIOLOGICAL SOIL DETECTOR

This is a continuation-in-part of prior application Ser. No. 10/842,599 filed on May 10, 2004.

FIELD OF THE INVENTION

The present invention relates to a biological soil detector and a method for using a biological soil detector.

BACKGROUND OF THE INVENTION

The general ability to detect pathogens on any of a variety of surfaces is desired. In food preparation, either in the commercial or home setting, the detection of pathogens on food preparation surfaces and the like is valuable to prevent cross-contamination of food items being prepared on the surface. Examples of contaminating materials may include bacteria, food products that contain bacteria (e.g. raw meat and its juices), or certain biological fluids. To prevent cross-contamination, it is desirable to determine the level of soil on certain surfaces such as household surfaces including kitchen and bathroom surfaces (e.g. counters, cutting boards, toilets) as well as room surfaces (e.g. floors, walls). In addition, an assessment of cleanliness is important for the surfaces of medical devices exposed to biological fluids during use. Examples of medical devices include the surfaces of endoscopes, catheters, and the like.

While kits are commercially available to test the cleanliness of certain surfaces, available kits typically require samples to be sent to an outside laboratory for analysis. The time involved in sending samples to an outside laboratory for analysis must be factored into the time required for the requester to receive a response. Additionally, culture methods are typically employed in the analysis for pathogens, thus requiring microbiology laboratory equipment and the expertise of trained microbiologists.

In health care fields, medical devices such as endoscopes, find utility in medical procedures that expose the devices to biological soil. Endoscopes, for example, are used in medical procedures within a patient's body in which the endoscope is inserted into the body either through a natural orifice or through a surgical opening. Endoscopes include a number of channels that may carry optical fibers for viewing areas in the body to facilitate the examination of organs, joints or body cavities and for conveying light to the area being viewed. Operating instruments such as electrosurgery probes or forceps may be passed through the channels of an endoscope, and the channels may also be used to deliver fluids or gas, or to provide suction or pass sampling catheters therethrough.

Virtually any part of the human body is accessible to an endoscope, and typical surgical sites include the ear, throat, urinary tract, lungs, intestines and the abdominal cavity. Endoscopes used in colonoscopy procedures permit the direct examination of the inside of the colon and large intestines for the presence of polyps, ulcers and inflammation. Foreign bodies such as polyps or tumors may be surgically removed through the endoscope.

As may be apparent, endoscopes and other medical devices are exposed to any of a variety of body soils during their uses in surgical procedures. Such soils include blood, fecal matter, cellular matter from various tissue, and the like, and any of these soils may provide sources of viruses or bacteria. Because of their use within the body, endoscopes must be thoroughly cleaned and disinfected following each use to ensure that all soiled surfaces are disinfected prior to using the medical device in subsequent medical or surgical procedures.

In a cleaning process employed in the United States on reusable endoscopes, the soiled endoscope is initially cleaned during a manual cleaning step to remove as much soil as possible from the surfaces of the instrument. Thereafter, a high level disinfection step is performed on the manually cleaned endoscope to render it ready for reuse. Typically, the manual cleaning step is performed by scrubbing the instrument with a cleaning brush or similar instrument. The manual cleaning step is performed until the brush no longer appears to pick up soil from the surfaces of the instrument. In the absence of an effective manual cleaning process, residual soil may remain on the surfaces of the instrument so that a risk for bacterial contamination may remain, thus increasing the possibility that the subsequent high level disinfection process may not be effective. Currently, there is no standard test device or methodology that provides a rapid determination of the efficacy of the manual cleaning step.

It is desirable to facilitate an ability to evaluate the efficacy of a cleaning or disinfecting process for any of a variety of surfaces, including the surface of endoscopes and other medical devices. It is desirable to provide a method that avoids extended incubation periods and facilitates the rapid identification of residual soil or the presence of certain pathogens. It is also desirable to provide an article or device that can be used in the performance of the foregoing method.

SUMMARY OF THE INVENTION

In some embodiments, the invention provides a biological soil detector, comprising:

A solid support member;

A specific indicator immobilized on the solid support member, the specific indicator comprising a material sensitive to the presence of blood; and The solid support and specific indicator positioned with respect to the detector to facilitate contact with a liquid that has been used to contact a surface.

In another embodiment, the invention provides a method for detecting bio soil associated with a surface, comprising:

Contacting the surface with a liquid;

After the liquid has contacted the surface, contacting the liquid with the solid support member and the specific indicator of the detector described herein; and Inspecting the solid support member for a detectable response to determine whether the specific indicator has interacted with biological soil.

In still another embodiment, the invention provides a biological soil detector, comprising:

A solid support member;

A specific indicator immobilized on the solid support member; and

The solid support and specific indicator positioned to facilitate contact with a liquid used to contact a surface.

As used herein, the terms used in the description of the various embodiments of the invention will be understood to have their ordinary and accustomed meaning unless stated otherwise. For convenience, specific definitions are provided for certain terms, such as the following:

"Biological soil" or "bio soil" refer to, by way of example, body fluids (e.g., saliva, blood, digestive fluids) fecal matter, cellular materials and tissue, microbial matter, bacteria, viruses, pathogens and other biological or biochemical materials including enzymes as well as partially or wholly digested foods. Sources of biological soil may vary but may include blood, human bodies, animal bodies, plant matter and various food products such as meats, poultry, dairy products which may, for example, be contaminated or which are at least partially digested and/or decomposed.

As used herein, "patient soil" refers to biological soil that remains on a medical device following the removal of the device from a human body.

A "specific indicator" refers to one or more chemical compounds that will interact with an enzyme or protein, such as those found in biological soil, to thereby provide a detectable response such as visible color changes or detectable changes in the fluorescent or luminescent properties of the specific indicator.

"Immobilized" refers to the retention of a chemical compound on a solid substrate in a manner that will resist removal of the compound from the substrate when the substrate is exposed to water, aqueous solutions, mechanical forces or the like.

Additional details of the preferred embodiments are provided in the remainder of the disclosure including the Detailed Description Of The Preferred Embodiment and the appended claims.

BRIEF DESCRIPTION OF THE DRAWINGS

In the description of the preferred embodiment, reference is made to the various Figures wherein reference numerals are used to identify features of the depicted embodiments with like reference numerals indicating like structures and wherein.

DETAILED DESCRIPTION OF THE PREFERRED EMBODIMENT

Figure 1A:
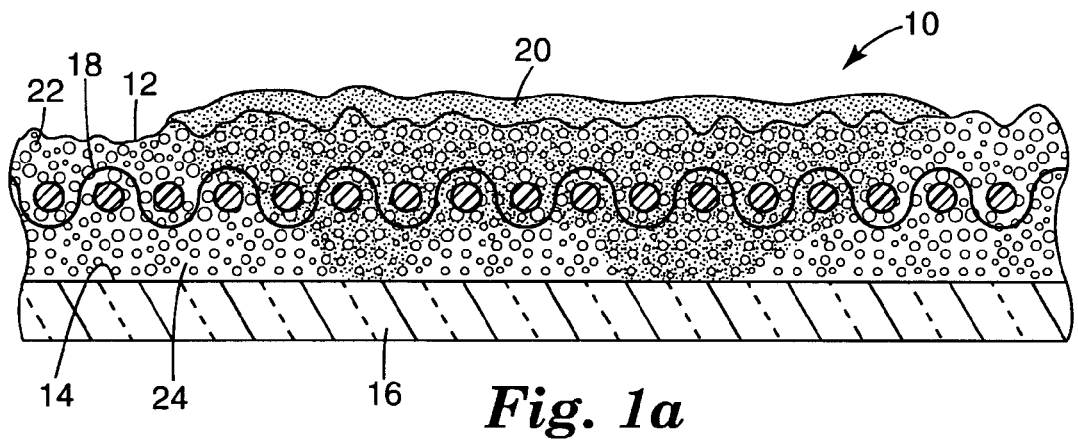
FIG. 1a is a side elevation, in cross section, of a portion of one embodiment of a solid support member according to the invention.

The present invention provides a detector and a method for the detection of biological soil. The detector of the invention utilizes one or more specific indicators immobilized on a solid support member wherein the specific indicators provide a detectable response when contacted with biological soil. The present invention generally relates to the detection of markers or analytes (e.g., detectable biochemical substances) that are indicative of the presence of biological soil. Detectable markers include components found in biological soil including any of a variety of proteins or enzymes found in or originating from a component of biological soil. The detector and method of the invention are suitable for use to determine the effectiveness of a cleaning step performed on a medical device. Additional uses for the device of the invention are also contemplated, such as the detection of bio soil on other surfaces including those used for food preparation or processing, for example.

In one aspect, the invention provides a means for associating the bio soil on a surface, such as a surface on a medical device, with a specific indicator immobilized on a solid support member. The specific indicator may be chosen for its sensitivity to components of the bio soil so that bio soil from a surface will react with the specific indicator to generate a detectable, relatively rapid, response. Detectable responses may be provided in the form of a color change on the surface of the solid support member or by a change in the fluorescent properties of the specific indicator. In various embodiments, the device of the invention includes the aforementioned solid support member which may be used to directly contact the surface being tested or may be indirectly used to test for the presence of bio soil by, for example, contacting the solid support member with a liquid that has been used to rinse the surface being tested. Typically, the latter embodiment will provide for the capture of the liquid within a receptacle that also holds the specific indicator immobilized on a solid support member so that the capture of the liquid will expose the solid support member and the immobilized specific indicator to the bio soil rinsed from the surface.

In some embodiments, the invention provides a means to determine the presence of biological soil on a medical device. One such application for the invention is the detection of biological soil following the manual cleaning step for an endoscope, for example. An endoscope permits direct viewing of areas within the body by insertion of the device through a natural orifice or through a small incision in the skin. Some endoscopes are rigid structures employing a series of lenses, while others are flexible and employ optical fibers to illuminate the area of concern within the body and to convey an image back to the eyepiece for the surgeon to see. Surgical operating instruments may be passed into the body through the channels of the endoscope in order to perform surgical procedures such as electrosurgery or the manipulation, grasping or crushing of structures within the surgical area. Endoscope channels may also deliver fluids or gases into the surgical site, provide suction or facilitating the positioning of catheters or laser light pipes. In the case of flexible endoscopes, an operating handle allows the surgeon to manipulate the tip of the endoscope to the desired location within the surgical site.

Following a use of an endoscope in a medical procedure, a manual cleaning process is employed to remove visible bio soil from the outer surface of the endoscope as well as from the inner surfaces or lumen of each exposed channel. After the manual cleaning step, the instrument may be disinfected using an appropriate high level disinfectant. The invention provides a means for detecting the presence of residual biological soil on an endoscope or other medical device to determine whether a cleaning step was successful or whether detectable soil is still present on the device so that the cleaning step must be repeated. If no soil is detected, the endoscope or other medical device is considered to be ready for high level disinfection.

Although the embodiments of the invention are typically described in connection with their use in the detection of bio soil on endoscopes, it will be appreciated that the invention is not to be limited to endoscopy applications. The invention may also be used to test other medical devices as well as surfaces used for the preparation, examination and/or treatment of patients in the healthcare industry. Additionally, the invention can be used in any of a variety of industries outside of the healthcare industry such as the food and beverage industry where there may be a concern that a surface might become soiled due to inadequate cleaning or the like. Moreover, the invention is useful in the testing of surfaces in homes and offices including bathroom surfaces, kitchen surfaces and the like. In its various aspects, the invention is suitable for rapidly testing any surface for the presence of a detectable amount of bio soil.

In at least one aspect, the invention provides a detector that includes a specific indicator with a means for contacting the specific indicator with a component of biological soil to produce a detectable response. As is further described herein, the detector can be provided in any of a variety of embodiments wherein the specific indicator may be selected to suitably detect biological soil and wherein the means for contacting the specific indicator with a component of biological soil can also be provided in any of a variety of forms. Embodiments of the invention and the various components thereof are further illustrated and discussed below.

In the various embodiments of the invention, a solid support member is provided along with a specific indicator immobilized on the solid support member. Referring to the various Figures, FIG. 1a illustrates an embodiment of a solid support member 10 having a first surface 12 and a second surface 14. In the depicted embodiment, the support 10 is a porous material comprising open areas or pores 22, and solid portions 24 extending between the pores 22. An optional backing 16 is affixed to the second surface 14 of the support 10. An optional scrim 18 extends through the support 10 to provide additional strength for the support 10 so that it can withstand significant stretching or pulling when, for example, the support is pushed through a channel in a medical device such as an endoscope. The scrim 18 may comprise any of a variety of reinforcing materials including woven, nonwoven or knitted materials.

A specific indicator chemistry is immobilized on the solid support member 10 in at least one area of the support. In the embodiment shown in FIG. 1a, the specific indicator chemistry is identified as the layer 20 associated, in part, with the first surface 12. While the specific indicator layer 20 is mainly associated with the first surface 12, the indicator may extend through the body of the support 10 (as indicated by the shaded portions of the support 10). It is contemplated that the indicator may be associated with the solid support member along a layer on a surface of the solid support member (e.g., layer 20), or the indicator may be associated in part with a surface of the solid support member, or the indicator may be mainly or completely disposed within the body of the solid support member 10. As used herein, "immobilized on," when referring to the placement of the specific indicator relative to the solid support member, will be understood to encompass all possible placements of the specific indicator relative to the solid support member and is not intended to be limited to the placement of the specific indicator at or on a surface of the solid support member. Additionally, more than one area of the solid support member may be associated with a specific indicator and the use of multiple (e.g., two or more chemically different) specific indicators on the same solid support member is contemplated within the scope of the invention.

Figure 1B:
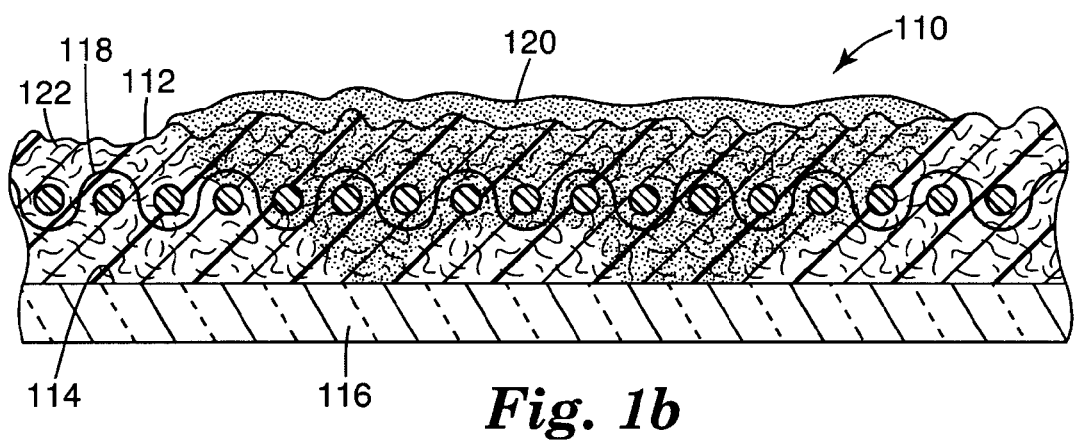
FIG. 1b is a side elevation, in cross section, of a portion of another embodiment of a solid support member according to the invention.

Referring to FIG. 1b, another solid support member 110 is illustrated in the form of a nonwoven material or fabric comprising an assembly of fibers 122 which may be oriented in a single direction or in a random manner. The nonwoven solid support member 110 may be held together in any manner known to those of skill in the art, including (1) by mechanical interlocking of the fibers 122; (2) by the fusing of thermoplastic or binding fibers, or (3) by the adhesive bonding of the fibers with an appropriate binder such as a rubber, starch, glue, casein, latex, or a cellulose derivative or synthetic resin.

As in the embodiment of FIG. 1a, the solid support member 110 of FIG. 1b includes a first surface 112 and a second surface 114. An optional backing 116 is affixed to the second surface 114 of the support 110. An optional scrim 118 extends through the support 110 to provide reinforcement so that the support 110 is able to withstand the stretching or pulling expected during use such as when, for example, the support 110 is pushed through a channel in a medical device such as an endoscope. Specific indicator chemistry is immobilized on the solid support member 110 in at least one area of the support. In the embodiment shown in FIG. 1b, the specific indicator chemistry is identified as the layer 120 associated, in part, with the first surface 112 but extending through the body of the support 110 (as indicated by the shaded portions of the support 110). In other aspects, the embodiments of FIGS. 1a and 1b are substantially the same.

Figure 1C:
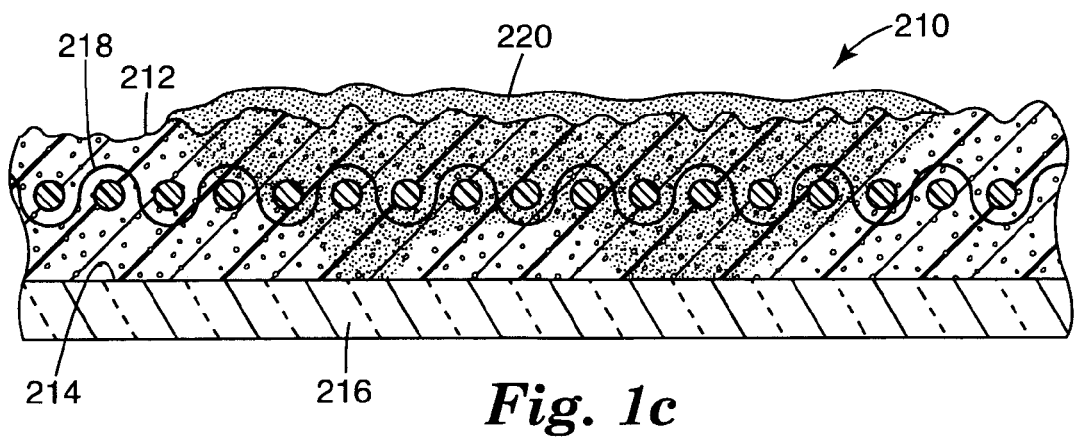
FIG. 1c is a side elevation, in cross section, of a portion of another embodiment of a solid support member according to the invention.

Referring to FIG. 1c, another solid support member 210 is shown, having a first surface 212 and a second surface 214. Optional backing 216 is affixed to the second surface 214 of the support 210, and optional scrim 218 extends through the support 210 to reinforce the support 210. Specific indicator chemistry is immobilized on the solid support member 210 in at least one area of the support. In the embodiment shown in FIG. 1c, the specific indicator chemistry is identified as the layer 220 associated, in part, with the first surface 212 but extending through the body of the support 210 (as indicated by the shaded portions of the support 210). The solid support member 210 may comprise any of a variety of materials capable of having a specific indicator layer 220 immobilized on the solid support member. Such materials are described elsewhere herein. In all remaining aspects, the embodiments of FIGS. 1a, 1b and 1c are substantially the same.

The solid support member in the foregoing embodiments of FIGS. 1a through 1c may be used, for example, as a single-use or disposable wipe for the detection of bio soil on various surfaces such as surfaces that have been in contact with food (e.g., food preparation surfaces, food or meat processing areas and the like), bathroom and kitchen sinks, counters, cutting boards, toilet surfaces, floors, walls, and any other surface where biological soil may be present. Such a wipe may be used dry (e.g., on a wet surface), or it may be wetted with water or an aqueous solution. In some embodiments, a cleaning or disinfecting solution may be incorporated into the wipe so that the cleaning or disinfecting of a surface may be performed at the same time the surface is being tested for bio soil. Accordingly, the invention provides a wipe that is useful in the evaluation of the cleanliness of a surface so that additional cleaning or disinfecting may be performed on the surface if the specific indicator interacts with a component of patient soil to provide an observable color change on the surface of the wipe or a change in the fluorescence of the surface of the wipe.

As noted, the solid support member is a substrate for the immobilization of a specific indicator. Suitable materials for the solid support member may be either a single base material having desirable surface characteristics, or a composite structure. If the solid support member is a single base material, suitable materials are polymers, inorganic, or mixed organic and inorganic surfaces that exhibit a contact angle with water of less than 90 degrees, preferably less than 50 degrees, and most preferably less than 10 degrees. Suitable materials include, but are not limited to, polymers containing the following functional groups: carboxyl groups and salts thereof, aldehydes, sulfonic acid and salts thereof, phosphonic acid and salts thereof, alcohol, primary amine, secondary amine, tertiary amine, amide, imide, quaternized ammonium, sulfonium, phosphonium, pyridine, cyclic amido (e.g. 2-pyrrolidinonyl, 2-piperidinonyl), oxyalkylene, and imidazole. Polymers or copolymers that contain or may be prepared to contain these functional groups include, but are not limited to, the following: carboxyl containing polymers such as, e.g., polymers and copolymers synthesized from acrylic acid and/or methacrylic acid including salts thereof; polyalkoxylates; poly(meth)acrylates; polyvinyl alcohol and copolymers, such as polyethylene-vinyl alcohol copolymer (e.g., available under the trade designation EVAL F101A from EVAL Company of America (EVALCA), Houston, Tex.); polyurethanes; polyureas; polyesters; polyamides, such as nylon 6,6; polyimides; polyethers; celluloses such as cellulose acetate, nitrocellulose, hydroxymethylcellulose, hydroxypropylcellulose; rayon; polyphosphate; polypeptide; polyacrylonitrile; polyacrylamide; polycarbonate; polyethersulfone; and combinations thereof.

Suitable inorganic materials include metal oxides, hydrates, and metal-hydroxyls (e.g. silicon hydroxyl (Si—OH) functional surfaces). Materials of construction that are both mixed organic and inorganic materials and suitable as supports include, but are not limited to, polymeric composites and ceramers, such as those based on copolymerization of metal alkoxides (e.g. tetraethoxyorthosilicate, n-hydroxypropyltrimethoxysilane) and organic monomers.

In embodiments where the solid support member is a composite structure, the first material or base material may be any polymeric, inorganic, or mixed organic and inorganic material to which the second material or coating material having desirable surface characteristics will adhere. Suitable base materials include, but are not limited to, polypropylene, polyethylene, polyvinylidene fluoride (PVDF), tetrafluoroethylene hexafluoropropylene vinylidene fluoride (THV), polyurethane, polyurea, polyester, polyvinyl acetate, polyamides, polyimides, poly(meth)acrylates, polyethersulfone, glass, silica, cellulosics, rayon, polycarbonate, polyvinyl alcohol, polystyrene, and combinations of the foregoing.

The base material may be modified via the application of suitable coating materials or surface treatments known to those skilled in the art to prepare a surface having a contact angle of water of less than 90 degrees, generally less than 50 degrees, and typically less than 10 degrees. Suitable coating materials may be prepared from monomers, polymers, or reactive metal alkoxides that may include one or more functional groups such as carboxylic acids and salts thereof, aldehydes, sulfonic acids and salts thereof, phosphonic acids and salts thereof, alcohols, primary amines, secondary amines, tertiary amines, amides, imides, quaternized ammonium, sulfonium, phosphonium, pyridine, cyclic amido groups (e.g. 2-pyrrolidinonyl, 2-piperidinonyl), oxyalkylene, ω-saccharinamidoundecylsiloxane (such as is described in Example 11 of U.S. patent application Ser. No. 10/713,174 filed Nov. 14, 2003), glycidyl, succinimido groups and imidazoles. Coating materials also may be prepared from monomers, polymers, or reactive metal alkoxides that do not contain functional groups including, but not limited to, alcohols, aldehydes, carboxylic acids, sulfonium, and phosphonium, but that may be subsequently modified by chemical reaction (e.g. oxidation, hydrolysis, degradation) to expose those groups at the surface. Coating materials may be applied using any known coating method including pattern coating (e.g. the coating material may be dropped in spots onto the base material). Surface treatment methods for preparation of a coating material suitable for a solid support member include but are not limited to: oxygen plasma, corona treatment, flame treatment, chemical vapor deposition, graft polymerization, and physical vapor deposition. As used herein, the term "coating" will be understood to include all constructions wherein a second material is applied to a first material on a solid support member such as continuous coatings, discontinuous coatings, coatings applied or arranged in a discontinuous pattern, coatings applied in a continuous pattern but arranged in a geometric or a non-geometric configuration, and the like.

The solid support member can be made to comprise materials that include: films, nonwoven materials such as cellulosic materials and materials that include a rayon/polypropylene nonwoven materials (e.g., those available under the trade designation Novonette 149-051 from BBA Nonwovens, Nashville, Tenn.) and nonwoven materials comprising rayon and polyester (e.g., 70% rayon/30% polyester), woven or knitted materials (e.g., prepared from cotton, rayon, or polymer materials), reticulated foams (e.g., polyurethane), open-celled foams (e.g., (meth)acrylate, polystyrene divinybenzene), porous ceramic inorganic frits (e.g., silica, alumina), fibers, particle-coated supports, sintered particles, sintered fibers, sponges (e.g., arranged in a brush like configuration), fiber bundles and membranes. In some embodiments of the invention, such as those to be inserted within a channel of a medical device (e.g., an endoscope), the solid support member comprises conformable, flexible, high integrity materials that are able to conform to and fit within the inner channels of a medical device while maintaining contact with the inner surfaces of the channel without experiencing structural failure (e.g., tearing or leaving remnants within the channel) when the solid support member is pushed and/or pulled through the length of the channel.

Suitable polymer membranes for use as the solid support member include those resulting from a phase inversion method in which an initially homogeneous polymer solution is cast and exposed to a cooler interface (e.g., a water bath or chilled casting wheel), and phase separation is induced in the solution film by lowering the temperature (thermally induced phase separation or "TIPS"). Suitable TIPS films or membranes may possess a broad range of physical film properties and microscopic pore sizes. They may be relatively rigid or non-rigid substrates prepared from any of a variety of polymers. TIPS membranes made according to the teachings of U.S. Pat. Nos. 4,539,256 and 5,120,594 are suitable for use in the invention and may comprise high density polyethylene (HDPE), polypropylene, polyvinylidenefluoride (PVDF), polyethylene-vinyl alcohol copolymer (e.g., available under the trade designation EVAL F101A from EVAL Company of America (EVALCA), Houston, Tex.), for example. The membrane may comprise a combination of materials such as a TIPS HDPE or a polypropylene membrane coated with a hydrophilic polymer (e.g., polyethylene-vinyl alcohol copolymer or EVAL) or a TIPS polypropylene support coated with a hydrophilic, strongly basic positively-charged coating such as polydiallyldimethylammonium chloride or a polymer incorporating quaternized dimethylaminoethylacrylate. The membrane also may comprise a strongly basic, positively-charged membrane comprising polyethersulfone copolymer with quaternary ammonium groups such as a membrane commercially available from Pall Corporation of Pensacola, Fla. under the trade designation "SB-6407." Other supports may comprise nonwoven materials prepared from non-rigid polymers and other materials including nylon materials such as positively charged Nylon 6,6 materials (e.g., those available under the trade designation Biodyne B from Pall Corporation, Pensacola, Fla. and those available under the trade designation Magnaprobe from GE Osmonics Labstore in Minnetonka, Minn.), a hydrophilic treated polypropylene membrane with 0.45 micron pore size, available under the trade designation GHP-450 from Pall Corporation, polyolefins (with a hydrophilic treatment); polyester, nitrocellulose, cellulose acetate, hydrophilic polytetrafluoroethylene (PTFE), polycarbonate, and the like. Combinations of materials may be used as a solid support member and the foregoing description is to be understood to include the aforementioned materials alone and in combination with other materials.

Regarding specific indicators, compounds suitable for use as specific indicators may be selected from any of a variety of materials capable of interacting with a component of bio soil to provide a detectable response. A consideration in the selection of a specific indicator is to select an indicator that will not react with cleaning solutions or components thereof or other substances that do not originate from biological soil, such as those substances that are introduced during the manual cleaning step for a medical device such as an endoscope. Individual compounds may be used as a specific indicator as well as combinations of compounds. Suitable specific indicators include, for example, 5-bromo-4-chloro-3-indolyl β-D-glucopyranoside; 5-bromo-4-chloro-3-indolyl β-D-galactopyranoside; 5-bromo-4-chloro-3-indolyl phosphate; 5-bromo-6-chloro-3-indolyl-β-D-glucopyranoside; 5-bromo-6-chloro-3-indolyl-β-D-galactopyranoside; 5-bromo-6-chloro-3-indolyl phosphate; 4-methylumbelliferyl-β-D-glucopyranoside; 4-methylumbelliferyl-β-D-galactopyranoside; 4-methylumbelliferyl-phosphate, esculin, orthophthaldialdehyde (OPA), polydiacetylenes as described in U.S. Pat. Nos. 6,395,561B1; 6,306,5989B1; 6,277,652; 6,183,722; 6,080,423 and WO 01/71317; Bradford assay based on the binding of Coomassie Brilliant Blue dye to proteins (available from Pierce Biotechnology Inc. of Rockford, Ill.); Lowry assay based on the reduction of the phosphomolybdic-tungstic mixed acid chromogen by a protein; Biuret assay based on the interaction of Cu+2 with protein in an alkaline solution; and the bicinchoninic acid (BCA) (available from Pierce Biotechnology Inc. of Rockford, Ill.) to detect the reduction of Cu+2 ions to Cu+1 in the presence of protein. Combinations of two or more of the foregoing immobilized on a solid support member are also contemplated within the scope of the invention. Additionally, when indolyl functional indicators are used in combination with nitro blue tetrazolium chloride (NBT) or other electron acceptors, faster development of color will occur in the presence of biological soil.

Enzyme activity maybe enhanced by the addition of monovalent or divalent metal ions, e.g., sodium, potassium, zinc, manganese, magnesium, calcium. Manganese salts can be incorporated in indicator formulations that include NBT to avoid the premature development of color (e.g., in the absence of bio soil).

In embodiments where the detector is provided as a wipe, the specific indicator typically comprises 5-bromo-4-chloro-3-indolyl β-D-glucopyranoside; 5-bromo-4-chloro-3-indolyl β-D-galactopyranoside; 5-bromo-4-chloro-3-indolyl phosphate; 5-bromo-6-chloro-3-indolyl-β-D-glucopyranoside; 5-bromo-6-chloro-3-indolyl-β-D-galactopyranoside; 5-bromo-6-chloro-3-indolyl phosphate; 4-methylumbelliferyl-β-D-glucopyranoside; 4-methylumbelliferyl-β-D-galactopyranoside and combinations of two or more of the foregoing. Nitro blue tetrazolium chloride (NBT) or other electron acceptors may be added to the foregoing specific indicators for faster development of color in the presence of biological soil.

In some embodiments, the invention provides a biological soil detector for the detection of blood using a specific indicator that is sensitive to the presence of blood and, more typically, to the presence of one or more components of blood. Blood components suitable which may be detected include, for example, proteins such as hemoglobin. Where the detection of hemoglobin is needed or desired, the specific indicator may comprise one or more indicators that provide a detectable change such as 3,3',5,5'-tetramethylbenzidine and other compounds capable of reacting with the product of peroxide and heme, materials useful in immuno assay based tests, tagged antibodies and the like. Suitable supports for such indicators include the supports mentioned herein. A commercially available specific detector and support for the detection of blood is the product available from Bayer Healthcare of Tarrytown, N.Y., under the trade designation "Multistix™." The Multistix products include a flexible plastic support on which a suitable specific indicator is immobilized. In some embodiments described herein, the Multistix product may provide a suitable support member and specific indicator that may be inserted into a retaining member, as described herein, to provide a biological soil detector according to the invention.

A number of different means of immobilizing the specific indicator to the support may be utilized; for example, adsorption, ion exchange, entrapment, microencapsulation, cross-linking, copolymerisation, entrapment and cross-linking, compounding, and covalent attachment. Adsorption of the indicator to the support occurs as a result of van der Waals, electrostatic and/or hydrophobic interactions between the indicator and support. Ion exchange results in binding of the indicator to the support due to electrostatic attraction between charges on the indicator and support. Entrapment implies mechanical capture of the indicator inside microscopic or macroscopic voids in the support. Microencapsulation or encapsulation involves covering the indicator chemistry either with a chemically different coating, usually for the purpose of protecting the indicator from external environments until exposure to a triggering physical or chemical event (e.g. sudden change in local relative humidity). Indicators can be crosslinked onto or into the support if they have reactive groups attached to them, either via surface-grafting or copolymerization into the bulk of the support, or they may be entrapped and subsequently cross-linked into the support.

Indicators also may be compounded as additives into polymeric supports via extrusion processing. Covalent attachment of indicators to the support may be achieved with solid support members functionalized with one or more ligands that react with functional groups on the indicator. Exemplary ligands include those mentioned in the Examples herein. It is desirable that the immobilization is accomplished in a manner that avoids steric hindrance in the reaction between the solid-phase indicator and the solution-phase reactant. Additionally, the immobilization should not inactivate the indicator. Particularly useful and convenient techniques are entrapment of the indicator chemistry in a microporous membrane and/or adsorption of the indicator chemistry to a support.

The selection of specific indicator may be influenced by the markers present in biological soil. Exemplary markers for detection include proteins, endotoxins, enzymes, and nucleotides such as adenosine triphosphate (ATP). Proteins can be useful markers for the presence of biological soil because of their ubiquitous presence in human secretions such as blood (e.g., hemoglobin) and in microbial cell components. The presence of an endotoxin would be representative of the lipopolysaccharide component of gram-negative bacteria. Detection of enzyme activity would signify the presence of enzymes that could be mammalian, plant or microbial in origin. Suitable enzymes for detection include, without limitation, galactosidases, phosphatases, glucosidases, lactosidases and others that are normally found in human secretions as well as those originating from a microbial or plant source. Other markers include sulfatases and fatty acid esterases.

Figure 7:
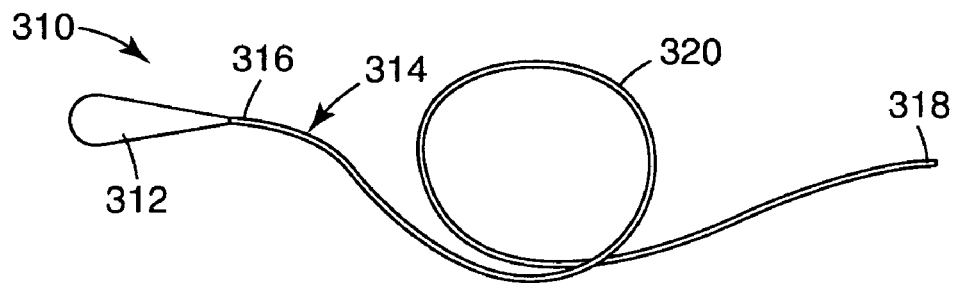
FIG. 7 is a perspective view of an embodiment of a detector according to the invention.

Referring to FIGS. 7-10, a detector 310 according to the invention is shown wherein each of the Figures incorporate different features which will now be described. The detector 310 includes a solid support member 312 associated with a retaining member 314 for retaining the solid support member 312 thereon. The retaining member 314 includes a first end 316 and a second end 318 and an elongate body portion 320 extending between the first end 316 and the second end 318. In the embodiment of FIG. 7, the solid support member is affixed to the first end 316 of the retaining member 314. Additionally, the length of the retaining member 314 may be varied as desired and is typically dimensioned in order to serve as a handle to facilitate contact between a specific indicator immobilized on the solid support member 312 and a surface to be tested. In this construction, the solid support member 312 may be positioned or extended to reach surfaces that may be out of reach or otherwise inaccessible. In other words, the user of the detector 310 may grasp the end of the retaining member 314 that is distal to the solid support member (e.g., second end 318) and use the length of the elongate body portion 320 of the retaining member 314 to reach a relatively remote or inaccessible surface with the solid support member and the specific indicator associated therewith. In some embodiments, the retaining member is dimensioned to fit within a channel of a medical instrument, such as a channel of an endoscope, to allow the solid support member 312 and the specific indicator to sample the channel walls for the presence of bio soil, including patient soil.

Figure 8:
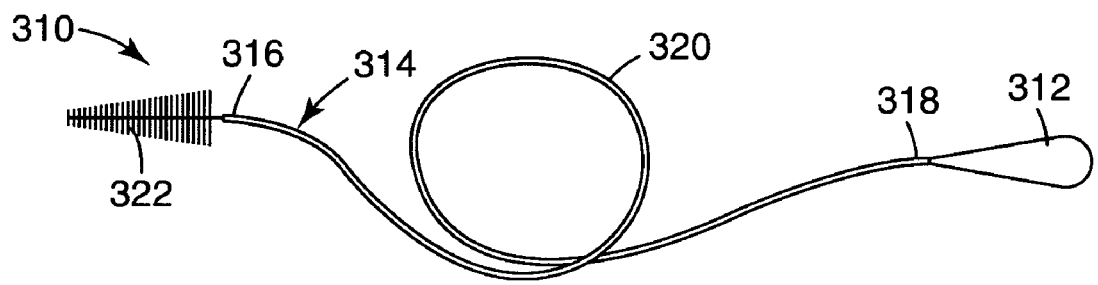
FIG. 8 is a perspective view of another embodiment of a detector according to the invention.

Referring to FIG. 8, the detector 310 includes solid support member 312 affixed to the second end 318 of the retaining member 314. Also, a cleaning brush 322 is provided and is affixed to the first end 316 of the retaining member 314. In this construction, the cleaning brush 322 provides a means for cleaning. In some embodiments, the brush 322 is sized and configured to clean a medical device such as an endoscope, and typically the brush 322 is sized and configured for cleaning within a channel of a medical device. Following a cleaning operation, the detector 310 may then be used to test for the remaining presence of bio soil on the device and especially within the channel(s) of the device.

In the foregoing embodiments, the retaining member is typically affixed to the solid support member in a permanent or non-removable manner. In other words, the attachment between the solid support member and the retaining member is not generally intended to permit detachment of these parts from one another. Regarding the manner of attachment, the solid support member and the retaining member may be attached to one another in any manner known to those of skill in the art including, without limitation, adhesive attachment, melt bonding, mechanical attachment (e.g., staples, buttons, snaps or the like). It is contemplated that all manners of attaching the solid support member to the retaining member are within the skill of those practicing in the field are encompassed within the present disclosure.

Figure 9:
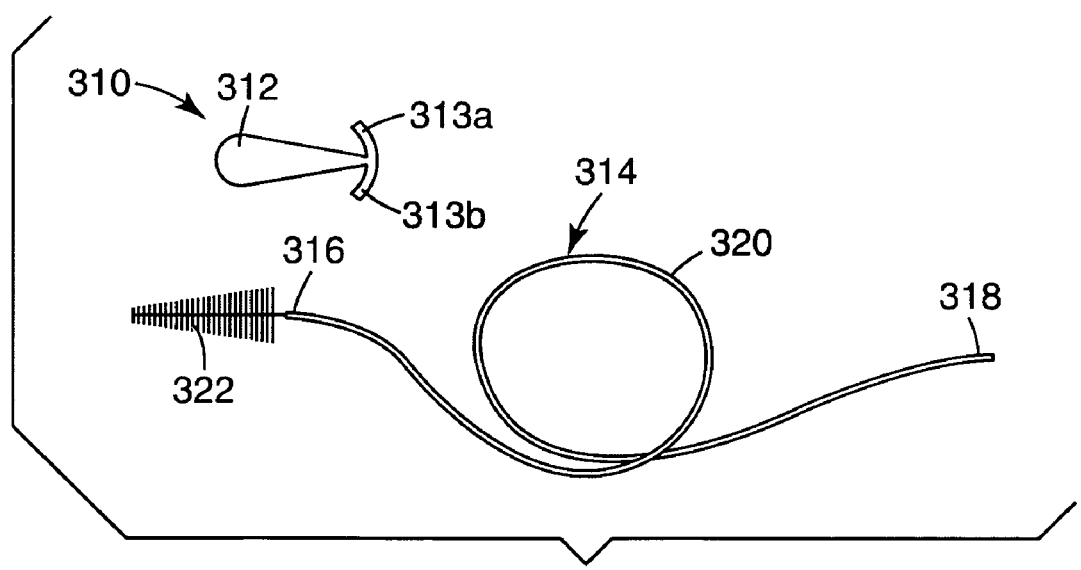
FIG. 9 is a perspective view of another embodiment of a detector according to the invention.
Figure 10:
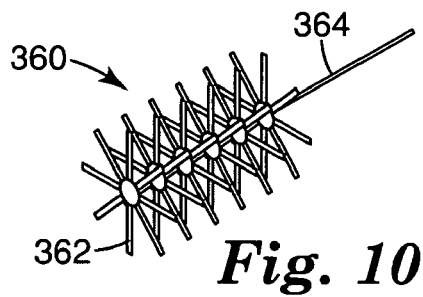
FIGS. 10-12 are views illustrating various embodiments of a retaining member and a solid support member for a detector according to the invention.

FIG. 9 shows still another configuration for the detector 310 wherein the brush 322 is associated with the first end 316 of the retaining member 314. The solid support member 312 is shown detached from the retaining member 314 to illustrate that the solid support member 312 may be releasably associated with the retaining member 314. In other words, the solid support member is provided as a separate component of the detector 310 that is detached from the retaining member 312 but which may be affixed to the retaining member 314 at any place along the length of the elongate body portion 320 or at either of the first end 316 or the second end 318. Moreover, the solid support member may be removed from the retaining member 314 following use so that the retaining member 314 and the brush 322 may be cleaned, disinfected and possibly sterilized as needed for use in a subsequent application. In the depicted configuration, the solid support member 312 includes wing-like projections 313a and 313b at an end of the solid support member. The wing-like projections 313a and 313b may comprise an inner reinforcing structure with a thin steel or metal wire to give each of the projections 313a and 313b some reinforcement and to provide a means for the solid support member 312 to be affixed to the retaining member 314 (e.g., by hand twisting of the wing-like projections around the outer circumference of the retaining member 314). Alternatively, the wing-like projections 313a and 313b may each be of a length to permit the two projections to be fastened to each other and the retaining member 314. It will be appreciated that the solid support member 312 and the retaining member 314 may be releasably affixed to one another by any known means (e.g., by use of a clip, adhesive or other fastener).

In the configuration of the detector shown in FIG. 9, the detector 310 may be provided with a single retaining member 314 and multiple solid support members 312 that have been pretreated with one or more specific indicators. In such an arrangement, the multiple solid support members 312 may include the same specific indicator(s) or different specific indicator(s).

Figure 11:
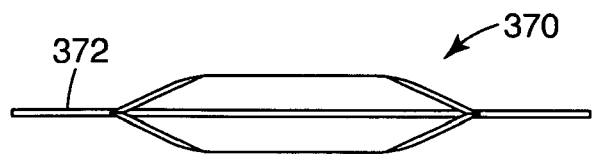

FIGS. 10-13a illustrate alternate configurations for the solid support member in the detector of the invention. FIG. 11 depicts a solid support member 360 positioned along retaining member 364. The solid support member 360 is comprised of a plurality of bristle-like members 362 projecting perpendicularly from the retaining member 364. In applications such as the detection of bio soil in a channel of a medical device, a sufficient number of such bristle-like members 362 are provided to ensure that the solid support member 360 samples substantially the entire surface of the channel when positioned therein.

FIG. 11 depicts another configuration of a solid support member 370 useful in the present invention. The support member is configured to permit bidirectional use in sampling the inner channel of an endoscope. In other words, the solid support member 370 may be pushed and/or pulled through the inner channel of a medical device in determining the presence or absence of detectable bio soil. Additionally, the solid support member 370 includes a relatively large surface area which facilitates the visual identification of a color change in the presence of bio soil.

Figure 12:

FIG. 12 depicts another configuration of a solid support member 380 useful in the present invention. As shown, the solid support member 380 may be made from a foam material that is configured to be directed through the inner channel of a medical device in a single direction. The solid support member 380 may be made using less material than, for example, the solid support member 370 in the embodiment of FIG. 11. However, the solid support member 380 includes a sufficient surface area to facilitate a rapid and relatively easy identification of a color change caused by the interaction of bio soil and the specific indicator associated with the solid support member.

Figure 13A:
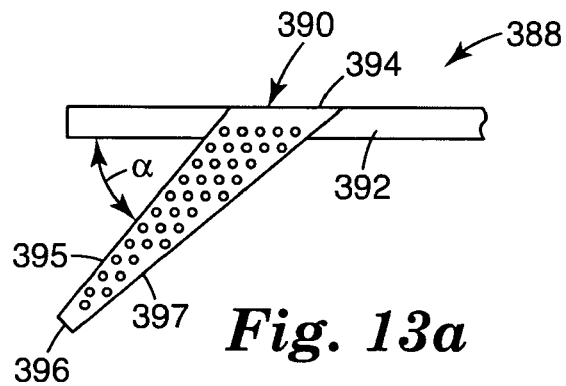
FIG. 13a is a side elevation, showing another embodiment of a feature of the invention.

FIG. 13a depicts another configuration of a detector 388 having a solid support member 390 that is flag-shaped comprising somewhat triangular shaped surfaces. The solid support member 390 is affixed to the retaining member 392 and comprises a first edge 394 attached to the retaining member and a second edge 396 remote from the first edge 394. The second edge 396 is shorter than the first edge 394 so that the side edges 395 and 397 extend between the first and second edges 394 and 394 in a non-parallel manner. Moreover, the angle (designated as α) formed between side edge 395 and the retaining member 392 is depicted as being about 45 degrees. In some embodiments, the angle may be different than is shown but will typically be less than 90 degrees, more typically less than 45 degrees, and often between about 20 and about 45 degrees. In this configuration, the solid support member 390 is useful in the sampling of a channel within a medical device. The angle α between the solid support member 390 and the retaining member 392 facilitate a uniform wrapping of the solid support member 390 around the retaining member 392 when inserted within the channel of a medical device, for example. It will also be appreciated that the solid support member 390 may be provided in a configuration in which the solid support member 390 is wrapped around the retaining member 392. In such a configuration, the size of the angle between side edge 395 and the retaining member 392 becomes less important in the overall performance of the detector 388.

Figure 13B:
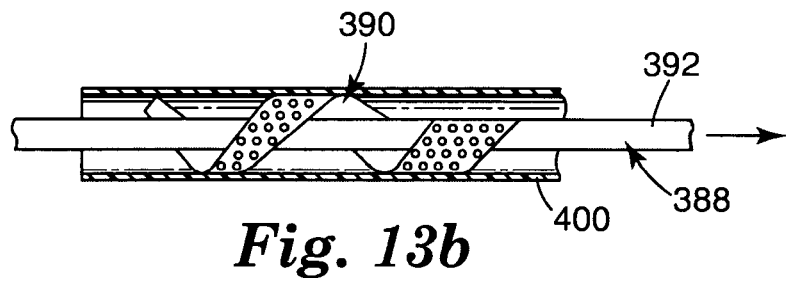
FIG. 13b is a side elevation, in partial cross section, illustrating a method of using the device of FIG. 13a, according to the invention.

FIG. 13b illustrates a use of the detector 388 in the sampling of the wall of a channel 400 in a medical device such as an endoscope. The solid support member 390 is of a length that facilitates the curling or wrapping of the solid support member in a 'cork-screw' or spiral pattern around the retaining member 392. The spiral wrapping of the solid support member 390 facilitates contact between a surface of the solid support member 390 and the channel walls along the entire channel surface as the detector 388 is moved through the channel 400 in the direction indicated by the arrow. In some embodiments, the length of the solid support member is about 50 mm.

Figure 14:
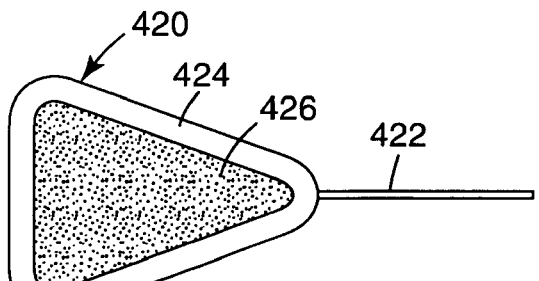
FIG. 14 shows another embodiment of a retaining member and a solid support member for a detector according to the invention.

Referring now to FIG. 14, a solid support member 420 is depicted as affixed to a retaining member 422, according to the invention. Solid support member 420 comprises a first area 424 comprised of a first material and a second area 426 comprised of a second material. Suitable first and second materials include those described elsewhere herein. In some embodiments, the first material can comprise a nylon nonwoven sheet, for example, and the second material can comprise a plurality of TIPS membrane segments affixed to the first material. In some embodiments, the first and second materials are affixed to one another using a hot melt adhesive applied (e.g., sprayed) to the TIPS segments. In this construction, a specific indicator may be immobilized within the second area 426. In embodiments where the specific indicator is colorimetric, the detection of bio soil can be enhanced if the first material is chosen to provide a background color that will visibly enhance the color contrast between the first and second materials upon a color change in the second material 426 caused by the interaction of the specific indicator with the bio soil.

Figure 15:
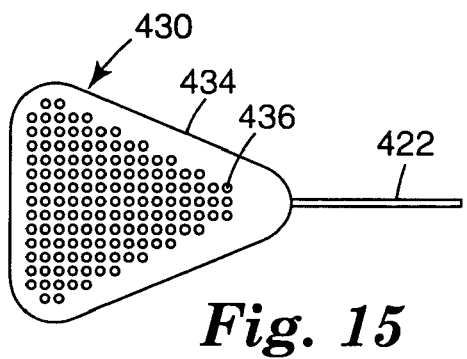
FIG. 15 shows another embodiment of a retaining member and a solid support member for a detector according to the invention.

Referring now to FIG. 15, a solid support 430 is depicted as affixed to a retaining member 432, according to the invention. Similar to the embodiment depicted in FIG. 14, solid support member 430 comprises a first area 434 comprised of a first material and a second area 436 comprised of a second material. In this construction, specific indicator may be immobilized within the second area 436 such as by printing the specific indicator on the solid support member within the second area 436. In embodiments where the specific indicator is calorimetric, the detection of bio soil can be enhanced if the first material is chosen to provide a background color that will visibly enhance the color contrast between the first and second materials upon a color change in the second material 436 caused by the interaction of the indicator with the bio soil.

In the detector constructions of the invention, a solution of the specific indicator may be coated onto the solid support member. The solvent may then be evaporated, thereby leaving the indicator compound immobilized on the solid support member. In some embodiments, the solid support member may be porous so that the specific indicator is retained within the pores of the solid support member through physical entrapment of the specific indicator within the pores, or by, for example, van der Waals forces, by hydrophobic and/or ionic interactions with the material used in the solid support member. In some embodiments, the solid support member may be treated prior to applying the specific indicator in order to render the solid support member hydrophilic and/or capable of covalently bonding with the specific indicator compound. A solution of the specific indicator may be coated uniformly over the entire surface of the solid support member or it may be coated onto the surface in a pattern covering some portion of the surface.

In some embodiments, the surface of the solid support member may be provided as uniformly white with the specific indicator immobilized on at least a portion of the white surface. In these embodiments, the white background will provide a sharp color contrast to the color generated by the reaction between the specific indicator and the bio soil and further facilitating the identification of a calorimetric reaction. In some embodiments, the surface of the solid support member may initially comprise a low fluorescence background to facilitate detection of a change in fluorescence upon a reaction between the specific indicator and bio soil.

Figure 22A:
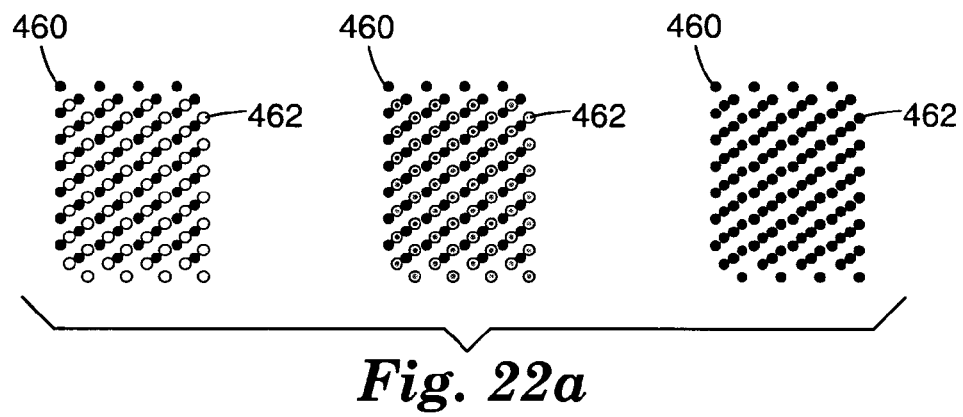
FIGS. 22a-22c are various views of patterns that may be employed in embodiments of the present invention.

In some embodiments, detection of a reaction between the indicator compound and biological soil may be enhanced if the indicator compound is applied to the surface of the support in a predetermined or ordered pattern. Moreover, background patterns on the surface of the solid support member may be provided to enhance or emphasize the presence of a calorimetric reaction, such as the patterns shown in FIGS. 22a-22c. In each of the Figures, moving from left to right, a progression is illustrated showing a change from an initial pattern to a final pattern facilitated by a calorimetric reaction. Referring to FIG. 22a, a series of small, closely grouped, darkly colored background circles 460 are provided along with a second pattern comprised of non-colored or lightly colored foreground circles 462. The foreground circles 462 may comprise visible circles of a lighter color than the background circles 460 or the foreground circles 462 may represent a colorless pattern of a specific indicator immobilized on the surface of a solid support member. Upon the detection of biological soil, a colorimetric reaction caused the foreground circles 462 to become visibly darker, so that the surface of the associated solid support member takes on a different appearance as the colorimetric reaction progresses to completion. In the pattern shown in FIG. 22a, the series of diagonally extending broken lines appears to become a series of unbroken lines occupying a rectangular area on the surface of the solid support member.

Figure 22B:
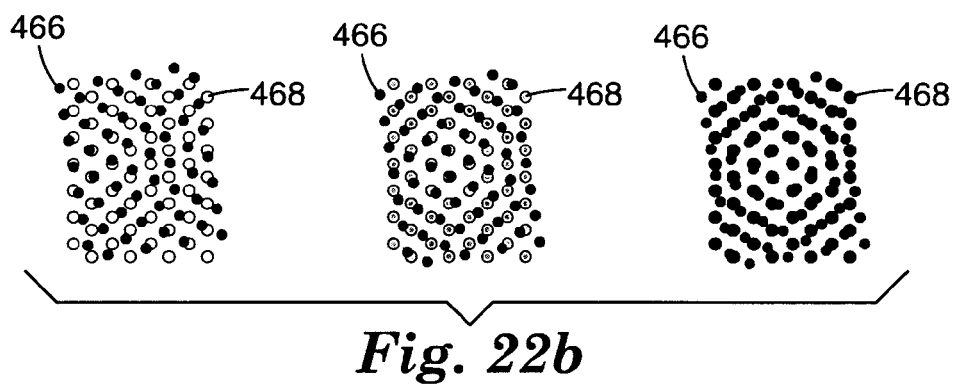
Figure 22C:
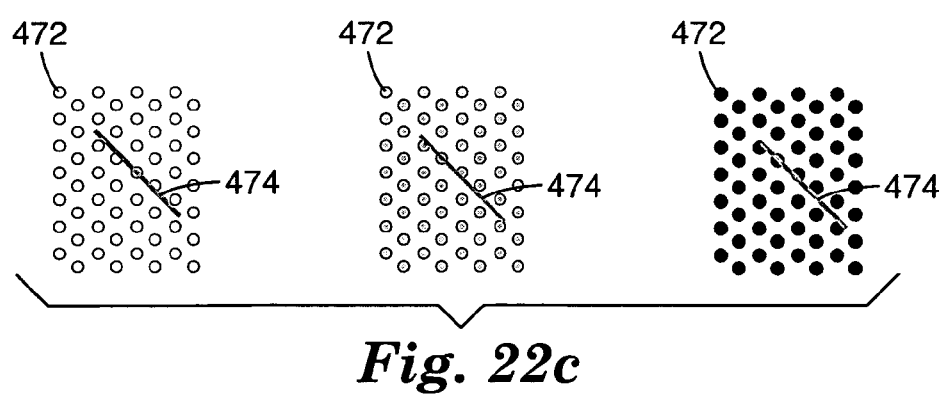

Similarly, FIG. 22b illustrates a pattern of foreground circles or dots 466 and background circles or dots 468 which progress into a geometric pattern as a colorimetric reaction progresses to completion. FIG. 22c illustrates a series or pattern of background circles 472 which may be initially presented as a lightly colored pattern or as a colorless and undetectable surface treatment applied to the solid support member. A printed or fixed mark, shown as a line segment 474 is provided over the background circles 472. As a colorimetric reaction progresses, the background circles become visibly darker until the appearance of the background circles 474 becomes the visually dominant feature, masking the presence of the segment 474. Patterns such as the foregoing are contemplated within the scope of the invention as a possible form for presenting the specific indicator on the solid support member to facilitate the visual recognition of a colorimetric reaction indicative of the presence of bio soil on a surface.

In embodiments of the invention, patterns like those described in relation to FIGS. 22a through 22c, are imprinted or otherwise affixed to the solid support member. The pattern represents an area on the solid support member that is to be visually inspected for a calorimetric response following the sampling of a surface. Typically, the area of the pattern will be large enough to facilitate the easy and quick visual identification of such a reaction, but the invention is not limited to any particular dimension or size of the area on the solid support member that has been treated with the specific indicator, whether in a pattern or otherwise.

As mentioned, the detector of the invention is useful in the detection of bio soil on a surface such as the surface of a medical device or any other surface which may have been exposed to bio soil such as food preparation surfaces, for example. To detect for the presence of bio soil on a surface, the detector described above with reference to FIGS. 7-14 may be used in a method comprising:

contacting the solid support member and the specific indicator with the surface;
withdrawing the solid support member from the surface; and
inspecting the solid support of the detector for a detectable response to thereby determine whether the specific indicator immobilized on the solid support has interacted with a component of biological soil.

In the foregoing method, the detector may be handled by a user grasping the detector along the axis of the retaining member (e.g., retaining member 314, FIG. 7), and extending the solid support member to a position on the surface being examined so that the solid support member and the specific indicator are in contact with the surface. Typically, the surface being tested and/or the solid support member will be at least slightly wet (e.g., with water). Contact with the surface at ambient temperature is generally sufficient to initiate an interaction between the bio soil (if present) and the specific indicator. When the detector is withdrawn from the surface, the solid support member may be inspected for a change in appearance such as a color change. In some embodiments, the solid support member is examined to detect changes in the fluorescence of the solid support member. Changes in color, appearance or fluorescence are indicative of the presence of bio soil. Typically, a change in appearance or fluorescence will be detectable in the solid support member in a relatively short period of time. Generally, a detectable change will be observed within 15 minutes or less, more typically less than 10 minutes, even more typically, less than 5 minutes and often less than one minute. As shown in the appended Examples, a detectable change is often apparent on the solid support member within 30 seconds or less. Additionally, the solid support member retains the specific indicator prior to any contact with biological soil and also retains the reaction products resulting from the interaction between the specific indicator and bio soil.

The detector of the invention may be used for the detection of bio soil on any surface. Exemplary of such as surfaces are those that contact food such as food preparation areas, food processing areas and the like. Any surface that potentially includes bio soil can be sampled with the detector of the invention such as bathroom and kitchen surfaces (e.g., sinks, counters, cutting boards, and toilet surfaces), floors and walls or the like. In an aspect of the foregoing embodiment, a cleaning or disinfecting solution may be incorporated into the solid support member so that the cleaning or disinfecting of a surface may be performed at the same time the surface is being tested for bio soil.

In some embodiments, the detector is useful for the detection of bio soil in the inner channels of a medical device. In the reprocessing of reusable endoscopes, for example, the detector of the invention is useful in the determination of the presence of residual bio soil following the cleaning steps normally employed for endoscope reprocessing. In particular, a soiled endoscope that has been used in a medical or surgical procedure is typically cleaned by an initial manual cleaning step to remove visible debris or bio soil from the surfaces of the instrument, including the surfaces of the inner channels. This is typically accomplished with a brush and a cleaning solution or solvent comprising an enzymatic cleaning compound applied to the surfaces of the endoscope. The surfaces of the endoscope are normally scrubbed with a brush to remove all of the visibly detectable bio soil from the surfaces of the medical device. Thereafter, the endoscope is subjected to a disinfection step using a high level disinfectant. After disinfection of the device with the high level disinfectant, the endoscope is thoroughly rinsed and dried so that it may be used again.

In order to evaluate the effectiveness of aforementioned manual cleaning step, the detector of the invention described above with reference to FIGS. 7-14 may be used to determine whether detectable bio soil remains on any of the surfaces of the endoscope prior to subjecting the endoscope to high level disinfection. In such a method, the detector of the present invention is used by first contacting the solid support member with a surface. In some embodiments, the retaining member of the detector is dimensioned to fit within the channels of the endoscope or other medical device to place the solid support member in contact with the walls of the channel. When used within a channel, the solid support member is typically chosen from very flexible materials so that the solid support fits within the channel in a manner facilitating contact between the specific indicator associated with the solid support member and the channel walls. The retaining member is normally of a sufficient length to ensure that the solid support member can be exposed to the wall of the channel along the entire length of the channel. Sampling of a channel wall in a medical device will typically be accomplished by sliding the detector through the channel in a single direction.

In another aspect of the invention, the detector is provided in a form that facilitates the detection of bio soil on the solid support member by rinsing the surface being tested with water or another liquid and thereafter capturing the rinse fluid in a manner that facilitates contact between the rinse fluid and the immobilized specific indicator on a solid support member.

Figure 2:
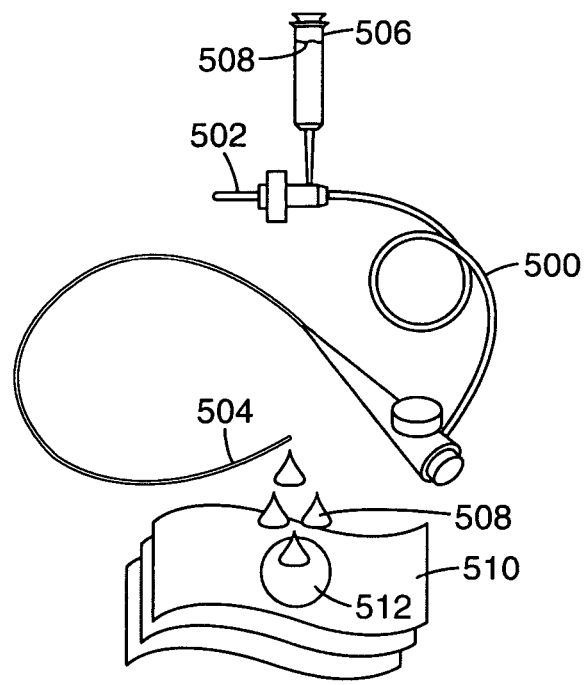
FIG. 2 is a perspective view representing an embodiment of a detector according to the invention.

Referring now to FIG. 2, another embodiment of a detector is depicted according to the invention and will now be described. An endoscope 500 is shown wherein one of its inner channels is being tested for the presence of bio soil. At one end 502 of the endoscope 500, a suitable sampling or rinsing fluid 508 is inserted into the channel of the endoscope 500 in a manner that facilitates the sampling of the entire length of the channel so that the fluid 508 exits the channel of the endoscope 500 at a second end 504 thereof.

The sampling fluid 508 may be any of a variety of liquids including tap water, deionized or distilled water, and solution or mixtures of various materials in a solvent, i.e., water, phosphate buffered saline, abrasives, neutralizing fluids. In some embodiments, abrasives added to the fluid will be those which are soluble in the solvent such as soluble salts, soluble polymer materials and the like. In other embodiments, undissolved solid abrasive particles may be used (e.g., silica). Where the surface being tested is part of a medical device used in medical testing, surgical or diagnostic procedures, it is generally desirable to utilize materials in the sampling fluid that will not adhere to the surface or that can be are readily removed from the surface prior to the device being re-used.

The sampling fluid is dispensed into the channel of the endoscope 500 with an appropriate amount of force to push the fluid through the channel. In some embodiments, a fluid dispenser such as a syringe 506 is used to dispense a predetermined amount of sampling fluid 508 into the channel of the endoscope 500. The sampling fluid 508 exits the second end 504 of the endoscope 500 and contacts the solid support member 510 with the specific indicator immobilized within an area 512 of the solid support member 510.

It will be appreciated that the invention is not to be limited to the sampling of an endoscope. Sampling fluid can be applied to any of a variety of surfaces and subsequently brought into contact with a specific indicator immobilized on a solid support member. The sampling fluid liquid may be brought into contact with the solid support member in any manner such as by the placement of the solid support member within the path of the sampling fluid as the fluid exits the channel or other surface being sampled. In some embodiments, the solid support member is simply placed within a stream of sampling fluid.

In some embodiments, the solid support member 512 is positioned within a receptacle that can also capture the sampling fluid 508 after the fluid has contacted the surface being tested, such as the channel of the endoscope 500. FIGS. 3-6 illustrate a receptacle 520 suitable for use in the present invention. It will be appreciated that receptacles used in the embodiments of FIGS. 3-6 are typically transparent to excitation and emission wavelengths for fluorescence and to visible wavelengths of light for visual detection.

Figure 3:
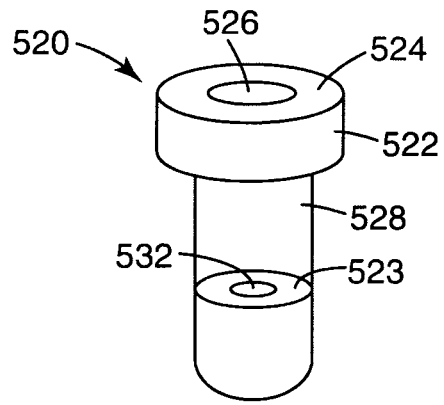
FIGS. 3-6 are perspective views of different embodiments of a feature of the embodiment depicted in FIG. 2.

In FIG. 3, the receptacle 520 is shown with a cap 522 having an open upper surface 524 defining an orifice 526 for allowing sampling fluid into the vial 528. In some embodiments, the upper surface 524 comprises a flexible material (e.g., silicone rubber) dimensioned to snugly fit over the end of a medical device (e.g., end 504 of endoscope 500) to allow sampling fluid to pass directly from the channel into the vial 528 and thereby avoiding the loss of sampling fluid by splashing or the like. Solid support member 530 is positioned within the vial 528 so that the area 532 treated with specific indicator is positioned to be exposed to the incoming stream of sampling fluid passing into the receptacle 520 through the orifice 526 in the upper surface 524 of cap 522. The solid support member 530 may be positioned within the vial 528 in a friction fit between the inner walls of the vial 528 and the edges of material comprising the solid support member 530. Alternatively, the solid support member 530 may be affixed within the vial 528 using an appropriate adhesive, for example. The specific indicator may provide a calorimetric response to the presence of bio soil or it may provide a fluorescent response that can be detected through the walls of the vial 528.

Figure 4:
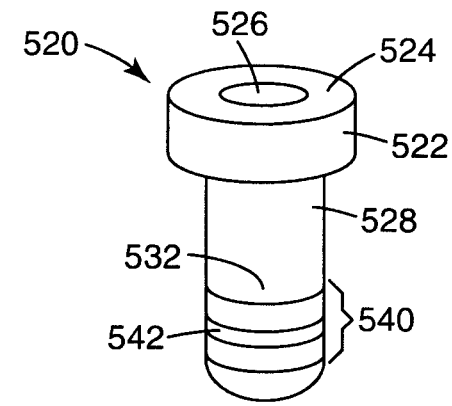

Referring now to FIG. 4, the construction of the receptacle is identical to that described for FIG. 3. However, the solid support member 540 is affixed to the inner wall of the vial 528, and specific indicator is immobilized on strip 542 within the solid support member 540. Typically, the solid support member 540 comprises a material as described herein wherein the solid support member 540 is affixed to the inner wall of the vial 528. Alternatively, the solid support member may comprise an adsorbent material deposited onto the inner wall of the vial 528 such as silica, cationic polymers (e.g., nylon), amine containing polymers, amine containing organosiloxanes and the like. The solid support member 540 is in intimate contact with the wall of the vial 528 to minimize any colorimetric or fluorescence absorbance by the sampling fluid that might partially obscure the calorimetric or fluorescent response of the specific indicator interacting with bio soil.

Figure 5:
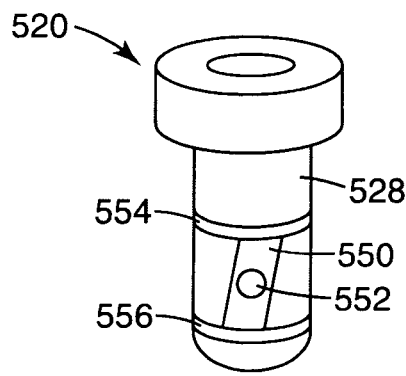

In FIG. 5, the solid support member 550 comprises a strip of material having an area 552 that comprises the immobilized specific indicator. The solid support member 550 is tethered to opposing sides of the wall of the vial 528 with a pair of adhesive strips 554 and 556. The solid support member 550 is positioned approximately centrally within the vial 528 so that the specific indicator in the area 552 is also in a centralized position within the vial to facilitate contact with the sampling fluid on both sides of the solid support member 550.

Figure 6:
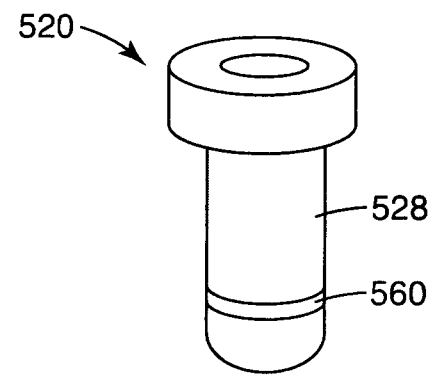

FIG. 6 depicts an embodiment of the invention in which the solid support member is the area 560 of the inner wall of vial 528. The specific indicator is immobilized on the solid support member 560 by chemically immobilizing the specific indicator on the walls of vial 528 so that a colorimetric reaction becomes visibly evident as a pattern that develops on the wall. Alternatively, the specific indicator may dissolve in the sampling fluid so that the fluid becomes colored or fluorescent as a reaction occurs between the specific indicator and bio soil in the sampling fluid. Typically, the vial 528 should provide a path length to enhance the limits of detection by either visual or fluorescent detection.

Figure 16:
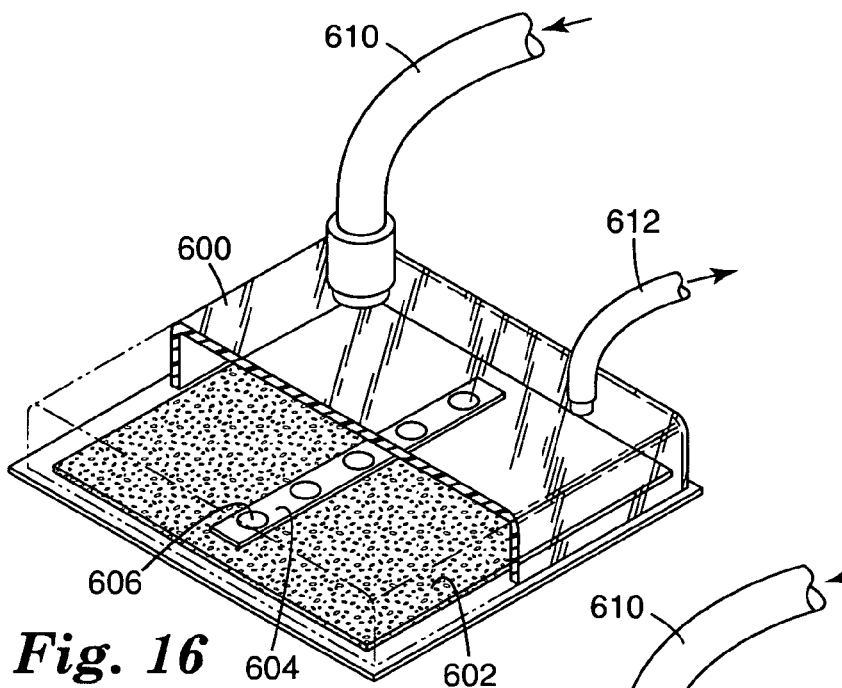
FIGS. 16-18 are various views of a feature of another embodiment of a detector according to the invention.
Figure 17:
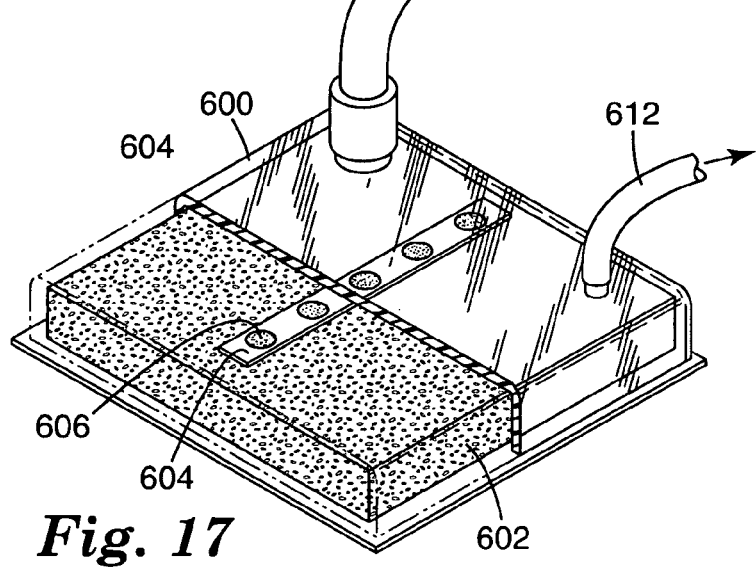
Figure 18:
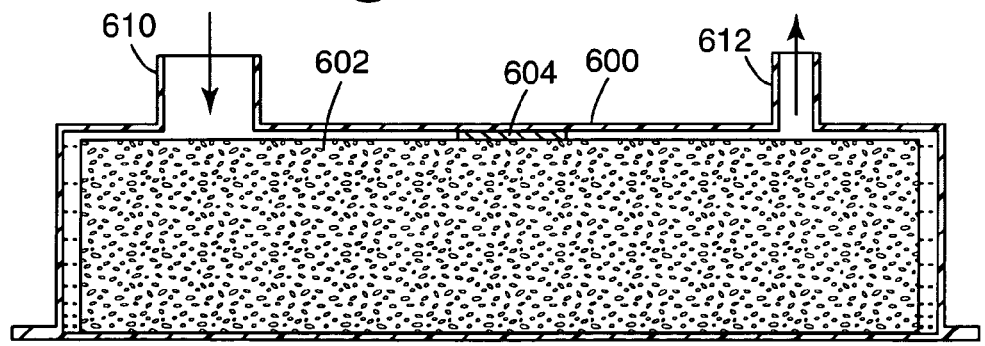

Referring to FIGS. 16-18, another embodiment of the invention is shown and will now be described. Here, another form of a receptacle 600 is depicted to capture sampling fluid drawn from a surface and into the container under a vacuum pull. FIG. 16 depicts the receptacle 600 prior to allowing sampling fluid therein. A sponge 602 is positioned in the container with a solid support member 604 associated with a surface of the sponge. Specific indicator is immobilized within the area 606 on the solid support member 604 comprised of the materials described herein. Inlet 610 connects with the source of sampling fluid (e.g., an endoscope), and the outlet 612 allows the container to be connected to a vacuum pump. In the progression depicted beginning with FIG. 16 and ending at FIG. 19, the container 600 (initially empty) receives sampling fluid therein through the inlet 610 under the draw of a vacuum connected to the outlet 612. The sponge 602 absorbs sampling fluid as it is drawn into the container 600. Depending on the volume of the sampling fluid used, the sponge 602 fills with the sampling fluid and swells, thereby filling the container 600 with the fluid-filled sponge 602 (see FIG. 18). The solid support member 604 and the specific indicator are in intimate contact with the sponge 602 so that the sampling fluid within the sponge 602 will contact the solid support member 604 and the specific indicator immobilized thereon. A calorimetric or fluorescent reaction is detected on the solid support member to indicate the presence of bio soil in the sampling fluid, as previously described.

Figure 19:
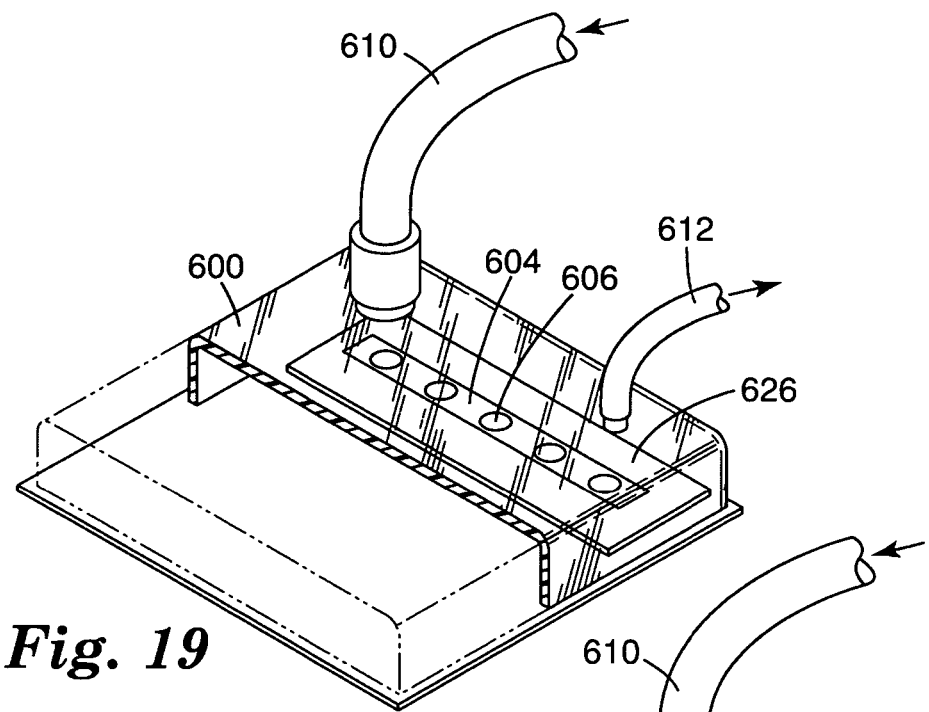
FIGS. 19-21 are various views of a feature of another embodiment of a detector according to the invention.
Figure 20:
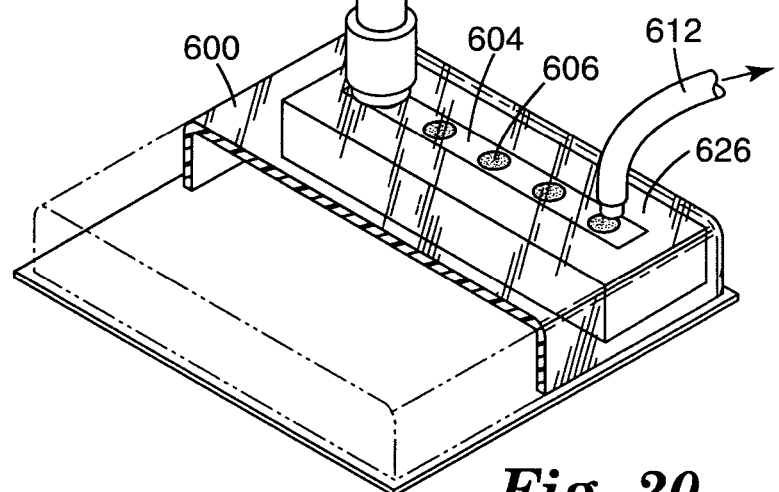
Figure 21:
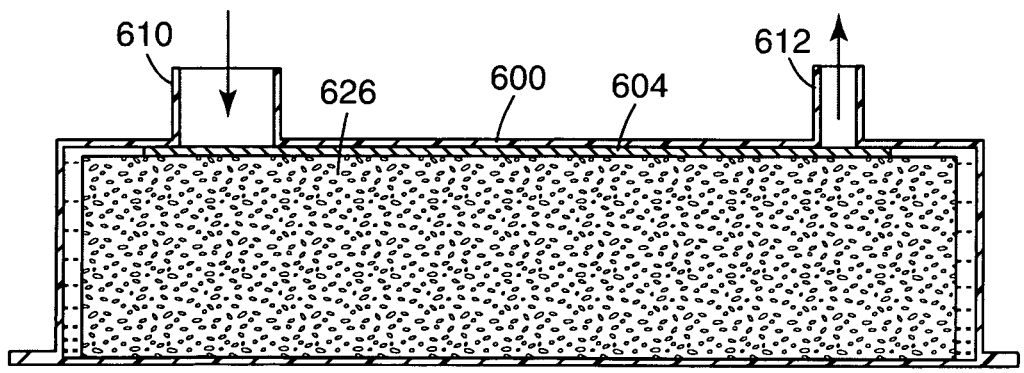

In another embodiment, FIGS. 19-21 illustrate a container with inlet 610 and outlet 612 ports, as previously described. The sponge 626, however, is substantially smaller than the sponge 602. Solid support member 604 with areas 606 of immobilized specific indicator is oriented within the container on top of the sponge 626. In the progression depicted in FIGS. 19-21, the sponge 626 swells up upon contact with the sampling fluid until the filled sponge 626 blocks the openings 610 and 612 (see FIG. 21). In all other respects, the embodiment of FIGS. 19-21 is the same as that described for FIGS. 16-18.

In some embodiments, the solid support member may be positioned on or within a retaining member such as the receptacle discussed in the foregoing embodiments. The retaining member will typically support the solid support member and the specific indicator with the retaining member positioned to facilitate contact between the liquid and the solid support member. It will be appreciated that the retaining member may be any structure or construction that holds and retains the solid support member to facilitate contact between the specific indicator and the liquid after the liquid has contacted the surface being tested. In some embodiments, the retaining member is a receptacle (e.g., as are described in FIGS. 3-6 and 16-21) capable of collecting and retaining the liquid, and the solid support and specific indicator are positioned within the receptacle to facilitate contact between the liquid and the specific indicator as the liquid is collected in the receptacle. In some embodiments, the retaining member comprises a structure capable of channeling the liquid therethrough, the solid support and specific indicator positioned within the retaining member to facilitate contact between the liquid and the solid support member when the liquid is channeled through the retaining member. Exemplary of structures capable of channeling the liquid therethrough include, for example, a tubular member to having a fluid inlet through which the liquid enters the retaining member and a fluid outlet through which the liquid exits the retaining member, the solid support and specific indicator typically positioned within the retaining member between the fluid inlet and the fluid outlet.

In some embodiments, an optional flow indicator is also provided to allow for a visual confirmation that liquid has passed through the detector. A flow indicator may comprise any of a variety of materials which change their appearance when wetted. In other words, the flow indicator will present a first appearance when the flow indicator is dry and a second appearance when the flow indicator has been exposed to a liquid. The optional flow indicator may comprise any suitable material or substance that will provide a discernable change in appearance from its dry state to its wetted state to indicate contact with a liquid. Suitable materials include absorbent materials such as woven materials, nonwoven materials, paper or cellulosic materials, and materials (including the foregoing) which have been treated with an appropriate dye or pigment capable of changing color when wetted. Commercial materials may be used as flow indicators in the present invention such as the specific gravity pad available in the Multistix® Reagent Strips available from Bayer Healthcare of Tarrytown, N.Y. The Multistix product provides a color change when wetted due to an apparent change in pKa of certain pretreated polyelectrolytes relative to ionic concentration. In one aspect of the invention, the flow indicator may be positioned adjacent to and downstream of the solid support member. In this arrangement of parts, a wetted flow indicator (e.g., presenting a second appearance) is also indicative of the specific indicator being wetted by a liquid. In another aspect of the invention, the flow indicator may be positioned upstream from the specific indicator so long as materials on the flow indicator will not migrate under the flow of liquid and interfere with the specific indicator. Further embodiments of the foregoing are discussed below. It will be appreciated that the flow indicator may be provided in any of a variety of configurations and may be positioned in any arrangement of parts with respect to the solid support member and the specific indicator. A tape with a water indicating dye is described in published U.S. Patent Application 20030096107, published May 22, 2003.

Figure 23:
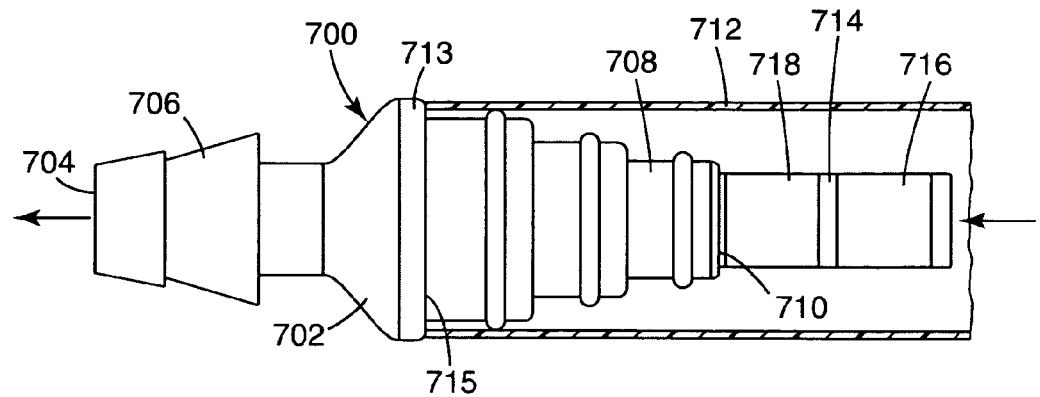
FIG. 23 shows a side elevation of another embodiment of a detector according to the invention.

In another embodiment of the invention, FIG. 23 illustrates one configuration of a retaining member 700 constructed to channel liquid therethrough and intended to permit the testing of the liquid for the presence of residual soil. In this embodiment, liquid will first be directed to a surface to dislodge residual soil following a cleaning step. The liquid will then be directed through the retaining member 700 which includes a body 702 having a flow inlet 710 disposed at a first end thereof. The retaining member 700 is constructed to direct a flow of fluid from the inlet 710 and through the body 702 to a fluid outlet port 704 located at a second end of the retaining member 700. The inlet port 710 is positioned at the end of inlet fitting 708 which is provided as a tapered friction fitting and is shown to be connected to a tube 712 which may be length of flexible tubing for directing the flow of fluid from the surface being tested to the retaining member 700. A solid support member 714 is associated with the retaining member 700 in a manner that ensures the flow of liquid through the tube 712 to the retaining member 700 will contact the support member 714 to expose the specific indicator, generally indicated by the area 716, to the liquid to thereby test for the presence of residual soil. In this embodiment, the solid support member is positioned at the inlet port 710. Areas of the solid support are pretreated with specific indicator immobilized thereon so that the presence of biological soil in the liquid will be indicated on the solid support member 714 by a visually observable change in color, a fluorescence measurement, or the like. Areas of the solid support member 714 that do not have specific indicator thereon may be provided with a "control" color that can be compared against a color change in the specific indicator. The same standard or control color can be provided elsewhere for the same comparison. For example, the control can be provided on a piece of paper supplied with the retaining member, on packaging, on another portion of the retaining member or the like.

A collar 713 supports the inlet fitting 708 and provides a surface 715 surrounding the base of the fitting 708. The diameter of the surface 715 is sized to abut the end of the tube 712, as shown. The inlet 710 provides the liquid with a path into the retaining member 700, through the body 702, and exiting through the flow outlet 704. The flow outlet 704 is disposed at the end of outlet fitting 706 which is a tapered friction fitting capable of mating with an end of a flexible tube (e.g., a drain tube) to direct the flow of fluid exiting the retaining member 700 to a drain, receptacle or other suitable disposal site.

The solid support member 714 may be associated with the flow inlet port 710 in any manner. In some embodiments, the solid support member 714 is permanently affixed to or is a permanent part of the retaining member 700 so that, upon being used once for the detection of bio soil, the entire retaining member is discarded in an appropriate fashion. In other embodiments, the solid support member 714 is reversibly positioned in the inlet port 710 in a manner that permits the removal of the solid support 714 from the retaining member 700 so that a new or fresh solid support may be used to replace a used solid support and so that the retaining member may be re-used following cleaning, disinfection and/or sterilization. If the solid support is a relatively rigid polymer or the like, the solid support member 714 may be inserted onto the inlet port 710 and releasably retained therein by a friction fit. Those skilled in the art will appreciate that the solid support member 714 may be affixed or associated with the inlet port 710 in any known manner such as by friction fit, adhesives, adhesive tapes, clips and the like.

In the embodiment of the retaining member 700 shown in FIG. 23, an optional flow indicator 718 is provided downstream of the specific indicator 716 so that a flow of fluid wetting the solid support member and the specific indicator can be readily detected. The optional inclusion of a flow indicator 718 is to provide a visual aid to facilitate the determination of whether liquid is actually flowing through the retaining member 700, and specifically facilitates a determination that the specific indicator has been in contact with a liquid. Moreover, the flow indicator 718 is normally positioned adjacent to the specific indicator 716 so that an indication of fluid flow on the flow indicator 718 provides an indication or verification that fluid has already reached the specific indicator 716.

While the flow of fluid in the foregoing retaining member has been conveniently described as flowing from inlet 710 to outlet 704, it will be appreciated that the foregoing retaining member will permit a flow of fluid from outlet 704 to inlet 710 as well. Moreover, the retaining member 700 will function according to the invention to permit the detection of bio soil regardless of the direction of flow through the member 700.

Figure 24:
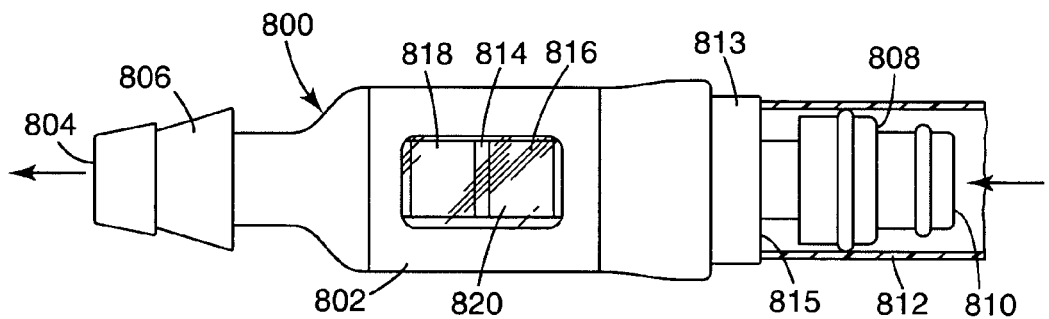
FIG. 24 shows a side elevation of another embodiment of a detector according to the invention.
Figure 25:
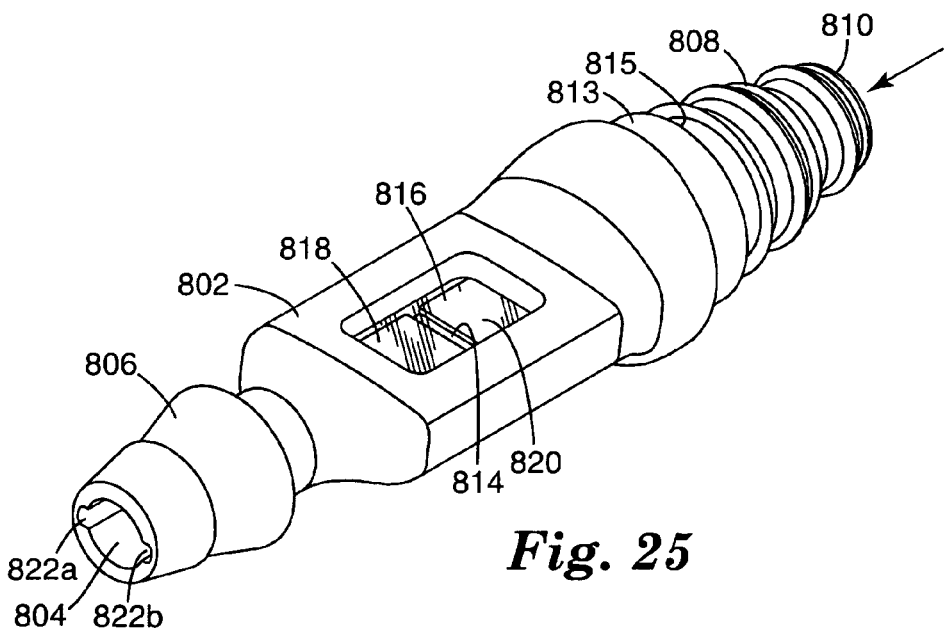
FIG. 25 shows a perspective view of the detector of FIG. 24.

Referring to FIGS. 24 and 25, still another embodiment of the invention is provided in the form of retaining member 800 which is constructed to channel liquid therethrough and is intended to permit the testing of the liquid for the presence of residual soil. In this embodiment, liquid will first be directed to a surface to dislodge residual soil following a cleaning step. The liquid will then be directed through the retaining member 800 which includes a body 802 having a flow inlet 810 disposed at a first end thereof which provides liquid with an entry path into the fitting. The flow inlet 810 is disposed at the end of inlet fitting 808 which is a tapered friction fitting shown here affixed to an end of a flexible tube 812 (e.g., a feed tube) to direct a flow of fluid that has been discharged from a medical instrument or from another surface to the inlet 810 and through the retaining member 800 to test for residual soil, as is discussed elsewhere herein. A collar 813 supports the inlet fitting 808 and provides a surface 815 surrounding the base of the inlet fitting 808. The diameter of the surface 815 is typically sized to abut the end of the feeder tube 812, as shown.

The retaining member 800 is constructed to direct a flow of fluid from the inlet 810 and through the body 802 to a fluid outlet port 804 located at a second end of the retaining member 800. The outlet port 804 is positioned at the end of outlet fitting 806. The outlet fitting 806 is provided as a second tapered friction fitting which may be connected to a flexible drain tube or the like to direct the flow of fluid from the retaining member 800 to a drain, collection receptacle or another suitable disposal site.

The flow of fluid through the retaining member 800 will normally be from inlet 810, though the body 802 and exiting through the outlet port 804. A solid support member 814 is positioned within the body 802 of the retaining member 800 in a manner that ensures the flow of liquid through the retaining member 800 will contact the support member 814 to expose the specific indicator, generally indicated within area 816, to the liquid to test for the presence of residual soil. The retaining member 800 is provided with a window 820 within the body 802 to permit the solid support member 814 to be viewed and inspected for a detectable change in the specific indicator 818 following exposure to a liquid. The window 820 may be provided in the body 802 in any manner. In some embodiments, the retaining member 800 is a molded part and the window 820 is provided as feature of the molded part. In some embodiments, the window may be punched or cut out of the body 802 of the retaining member 800. In either of the foregoing cases, the window 820 is typically covered with a transparent film or the like to permit an observer to view the specific indicator therethrough while preventing the flow of fluid from exiting through the window 820. In other embodiments, the entire body 802 of the retaining member 800 may be made of a transparent plastic or polymeric material which permits direct viewing of the solid support member and the specific indicator without the need for a window. Retaining member 800 also includes an optional flow indicator 818 downstream from the specific indicator 816 and also visible through the window 820.

The solid support member 814 may be positioned and retained within the body 802 of the retaining member in any known manner. In some embodiments, it is contemplated that the solid support member 814 will be affixed indefinitely within the body 802 of the retaining member 800 so that the fitting, after being used in the detection of bio soil, will be disposed of in an appropriate fashion. In other embodiments, it is contemplated that the solid support member 814 is releasably retained within the body 802 of the retaining member 800. In such an arrangement, the solid support member 814 may be removed from the body 802 and discarded, and the retaining member 800 may then be cleaned, disinfected and/or sterilized in an appropriate fashion so that it may be used again.

In some embodiments, the retaining member 800 is provided in a configuration that facilitates the direction of fluid flow therethrough and which directs fluid to the solid support member 814 as the fluid passes through the body 802 of the member 800. For example, the inner lumen or channel extending through the retaining member may include striations or channels therealong that facilitate the travel of liquid through the member 800 and which are configured to direct the flow of fluid to the solid support member 814 to first contact the specific indicator 816 before exiting the member 800 through the exit port 804. Another aspect of the invention includes microstructured arrays along the walls of the inner channel through the member 800, also configured to direct the flow of liquid through the inner surfaces of the retaining member to ensure that the solid support member and the specific indicator are exposed to the liquid and to any bio soil that may be present therein.

In the perspective view of FIG. 25, a pair of opposed slots or tracks 822*a* and 822*b* are provided within the retaining member 800 so that the solid support member 814 may be positioned within the tracks 822 and inserted into the body 802 through the flow outlet 804 and positioned within the body 802 so that the specific indicator and the optional flow indicator can be viewed through the window 820. It will be understood that the solid support member 814 may be positioned within the body 802 of the retaining member 800 in any manner so long as the support 814 is retained within the body of the fitting 800 without becoming easily dislodged by, for example, the flow of liquid through the body 802. Suitable means for retaining the solid support member 814 within the body 802 include without limitation friction, adhesives, adhesive tapes, clips, and the like. In this manner, the solid support member and the specific indicator are positioned to facilitate contact with a liquid that has been used to contact a surface for the purpose of detecting the presence of residual soil on a surface of a medical device or on another surface.

While the flow of fluid in the foregoing retaining member has been conveniently described as flowing from inlet 810 to outlet 804, it will be appreciated that the foregoing retaining member will permit a flow of fluid from outlet 804 to inlet 810 as well. Moreover, the retaining member 800 will function according to the invention to permit the detection of bio soil regardless of the direction of flow through the member 800.

Those skilled in the art will also appreciate that the foregoing embodiments shown in FIGS. 23-25 and discussed herein are merely exemplary of devices within the scope of the present invention. Other devices are contemplated and the invention is intended to encompass any device designed to sample a stream of liquid in which a specific indicator is positioned to contact the liquid after the liquid has contacted a surface to be tested. The specific configurations of such devices may include the general features of the foregoing devices of FIGS. 23-25 such as a flow inlet, a flow outlet, and a body portion which directs the flow of liquid from the inlet to the outlet in a manner that facilitates the contact of the liquid with a specific indicator immobilized on a solid support member.

As mentioned, the use of a sampling fluid with the foregoing components provides a method for detecting bio soil associated with a surface, comprising:

Contacting the surface with a liquid;

After the liquid has contacted the surface, contacting the liquid with the solid support member and the specific indicator; and Inspecting the solid support member for a detectable response to determine whether the specific indicator has interacted with biological soil.

In this aspect of the invention, liquid is used to contact the surface being sampled, to loosen and dislodge bio soil retained on the surface, and thereafter flush the dislodged soil into a vessel where the bio soil may interact with a specific indicator. The liquid is able to probe all of the portions of the surface being sampled including the spaces within joints or connection areas where bio soil may become entrapped. After the liquid has made contact with the surfaces being sampled, it is brought into contact with the specific indicator immobilized on a solid support, as described herein. In some embodiments, the biological soil detector may utilize a liquid in a passive mode wherein the liquid is delivered to the surface and thereafter brought into contact with the specific indicator without assistance. In some embodiments, the biological soil detector is provided with a vacuum pump to assist in the delivery of liquid to the surface of the solid support material. In other embodiments, fluid may be pushed or pumped into the detector (e.g., with a syringe or pump). In such embodiments, the delivery of fluid into the detector may be accomplished using constant pressure or pulsed pressure to drive or direct the fluid or liquid into contact with a specific indicator. The use of liquid to loosen bio soil from all potentially contaminated surfaces in a channel of a medical device can facilitate the sampling of channels that are too small to be directly probed with the solid support member affixed to a retaining member (e.g., air and water channels of an endoscope), as described herein. Moreover, the vacuum driven embodiments described above with reference to FIGS. 16-21 should typically be compatible with hospital vacuum systems.

It will also be appreciated that the foregoing device and method of use are not limited to being used in the detection of bio soil on medical devices such as endoscopes. Other surfaces, such as surfaces that have contact with food, may also be sampled to determine the presence or absence of biological soil. Any surface may be sampled for the presence of bio soil using the described devices and methods of the present invention.

Additional features of the preferred embodiments are further described in the following non-limiting Examples.

EXAMPLES

| Acronym | Trade Name | Generic Name | Source/Address |
|---|---|---|---|
| | | Glossary | |
| | | Substrate chemistries (specific indicators) | |
| BCIP/NBT | | 3-Part Phosphatase Substrate System containing 5-bromo-4-chloro-3-indolyl phosphate, p-toluidine salt, nitro blue tetrazolium chloride and TRIS buffer | Kirkegaard & Perry Laboratories, Inc, Gaithersburg, MD |
| | NBT/BCIP 1-Step ™ Solution | Nitro blue tetrazolium chloride/5-bromo-4-chloro-3-indolyl phosphate, p-toluidine salt | Pierce Biotechnology, Inc., Rockford, IL |
| X-glc or X-chemistries | | 5-bromo-4-chloro-3-indolyl β-D-glucopyranoside | Biosynth AG, Inc., Staad, Switzerland |
| BCI-gal, X-gal or X-chemistries | | 5-bromo-4-chloro-3-indolyl β-D-galactopyranoside | Kirkegaard & Perry Laboratories, Inc. or Biosynth AG, Inc. |

-continued

Glossary

| Acronym | Trade Name | Generic Name | Source/Address |
|---|---|---|---|
| BCIP, X-phos or X-phos-p-tol or X-chemistries | | 5-bromo-4-chloro-3-indolyl phosphate, p-toluidine salt | Biosynth AG, Inc. |
| NBT | | Nitro blue tetrazolium chloride | TCI, Tokyo, Japan |
| | Magenta ™-β-D-glc | 5-bromo-6-chloro-3-indolyl-β-D-glucopyranoside | Biosynth AG, Inc. |
| | Magenta ™-β-D-gal | 5-bromo-6-chloro-3-indolyl-β-D-galactopyranoside | Biosynth AG, Inc. |
| | Magenta ™-phos p-tol | 5-bromo-6-chloro-3-indolyl phosphate, p-toluidine salt | Biosynth AG, Inc. |
| | | 5-bromo-6-chloro-3-indolyl phosphate, disodium salt | Biosynth AG, Inc. |
| 4-MU-β-D-glc | | 4-methylumbelliferyl-β-D-glucopyranoside | Biosynth AG, Inc. |
| 4-MU-β-D-gal | | 4-methylumbelliferyl-β-D-galactopyranoside | Biosynth AG, Inc. |
| 4-MU-phos | | 4-methylumbelliferyl-phosphate, p-toluidine salt | Biosynth AG, Inc. |
| | | esculin | Sigma-Aldrich, St. Louis, MO |
| OPA | | orthophthaldialdehyde | Pickering Laboratories, Mountain View, CA |
| | Coomassie Plus□ | Protein Assay Reagent | Pierce Biotechnology Inc., Rockford, IL |

Enzymes

| | | Alkaline phosphatase (Sigma-Aldrich: 4000 units/mg) (Calbiochem: 35,820 units/mL) (1 unit of activity = amount of enzyme needed to hydrolyze 1 micromole of p-nitrophenyl phosphate/minute at 25° C., pH = 9.6) | Sigma-Aldrich, St. Louis, MO or Calbiochem, La Jolla, CA |
|---|---|---|---|
| | | β-glucosidase | Sigma-Aldrich or Worthington Biochemical Corp., Freehold, NJ |
| | | β-galactosidase | Worthington Biochemical Corp. or Sigma-Aldrich |
| | | *Pseudomonas aeruginosa* MBL 0484 culture | Microbiologics, St. Cloud, MN |
| BSA | | Bovine serum albumin | Sigma-Aldrich Chemical Co. |
| | | Calf serum | HyClone, Logan, UT |

Solvents

| Acronym | Trade Name | Generic Name | Source/Address |
|---|---|---|---|
| DMF | | dimethylformamide | Sigma-Aldrich |
| IPA | | Isopropyl alcohol | Sigma-Aldrich |
| MEK | | Methylethylketone | Sigma-Aldrich |

Support materials and coatings

| | Metricel SB-6407 | Copolymer of quaternary ammonium-functional polymer and polyethersulfone | Pall Corporation, East Hills, NY |
|---|---|---|---|
| | Biodyne B | Cationic nylon 6,6 | Pall Corporation East Hills, NY |
| | GHP-450 | hydrophilic treated polypropylene membrane with 0.45 micron pore size | Pall Corporation, East Hills, NY |
| | Magnaprobe | Positively charged nylon membrane | Osmonics, Minnetonka, MN |
| HDPE | FINATHENE 7208 | High density polyethylene | ATOFINA, Houston, TX |
| | | Silica Gel Glass Backed TLC Plates (2.54 cm by 7.62 cm)(1 inch by 3 inches) | Whatman Inc., Clifton, NJ |
| EVAL or EVOH | EVAL ™ F101A | Polyethylene-poly(vinyl alcohol) copolymer | EVAL Company of America (EVALCA), Houston, TX |

-continued

Glossary

| Acronym | Trade Name | Generic Name | Source/Address |
|---|---|---|---|
| PP | 51S07A | Polypropylene | SUNOCO Chemicals, Polymer Division, Pittsburgh, PA |
| PDAMAC | | Poly(diallyldimethylammonium) chloride | Sigma-Aldrich |
| TIPS | | Thermally induced phase separated Microporous membrane | U.S. Pat. No. 4,539,256 (Ex. 23) and 5,120,594 |
| | Novonette 149-051 | Rayon/PP Nonwoven | BBA Nonwovens, Nashville, TN |
| | | 70% rayon, 30% polyester nonwoven | Ahlstrom Windsor Locks LLC, Fiber Composites Division, Windsor Locks, CT |
| | | ω-saccharinamidoundecyltrichlorosilane | U.S. Patent Application No. 10/713174 (Ex. 11) |
| | | (N-trimethoxysilylpropyl) polyethyleneimine | United Chemical Technologies, Inc., Bristol, PA (Currently available from Gelest, Inc. Morrisville, PA) |
| | | 3-aminopropyltriethoxysilane | OSi Specialties North America, a Witco Company, South Charleston, WV(Currently available from Gelest, Inc.) |
| | | N-trimethoxysilylpropyl-N,N,N-trimethylammonium chloride | Huls America, Bristol, PA (Currently available from Gelest, Inc.) |
| | | Buffers, solvents, additives, wetting agents | |
| | Tween 80 | Polyoxyethylene (20) sorbitan monooleate | ICI Surfactants, Wilmington, DE |
| PBS | | Phosphate buffered saline, pH 7.4 | Examples 17, 20 |
| TRIS | | tris(hydroxymethyl) amino methane Iron buffer | Sigma-Aldrich Kirkegaard & Perry Laboratories, Inc. |
| | | 1,2-propanediol | J.T. Baker, a Division of Mallinckrodt, Phillipsburg, NJ |
| | | glycerol | Sigma-Aldrich |
| $FeCl_3$ | | Ferric Chloride | Sigma-Aldrich |
| $MnCl_2$ | | Manganese Chloride | Sigma-Aldrich |
| $MgCl_2$ | | Magnesium Chloride | Sigma-Aldrich |
| HCl | | Hydrochloric Acid | J. T. Baker, a Division of Mallinckrodt |
| GPS | | 3-glycidoxypropyltrimethoxysilane | OSi Specialties North America, a Witco Company (Currently available from Gelest, Inc.) |

Example 1

A solution was made using BCIP/NBT 3-Part Phosphatase Substrate System (Kirkegaard & Perry Laboratories, Inc.) by combining 12.5 μL of BCIP, 50 μL of NBT, 50 μL of TRIS buffer, and 37.5 μL of water. The rough side of Biodyne B film was spotted using a micropipette to place 5 μL of the solution made from the BCIP/NBT 3-Part Phosphatase Substrate System and air dried for 30 minutes. The spotted film was respotted with 5 μL of alkaline phosphatase (Calbiochem) at a concentration of 3.6 units/mL.

After 26 seconds, a blue-purple spot appeared indicating the presence of alkaline phosphatase.

Example 2

A 0.05 M TRIS buffer at pH=8.9 was prepared by mixing 50 mL 0.1 M TRIS in deionized water with 7 mL 0.1N HCl and 43 mL of deionized water. A first solution was prepared by combining 25 mg BCIP with a mixture of 3 mL 1,2-propanediol, 2 mL glycerol, and 5 mL 0.05 M TRIS buffer (pH=8.9). A second solution was prepared by combining 50 mg NBT with 3 mL 1,2-propanediol, 2 mL glycerol, and 5 mL 0.05 M TRIS buffer (pH=9). Next 100 μL of the first solution was mixed with 100 μL of the second solution, 100 μL of 0.1 mg/mL $MnCl_2$ in water, and 1 mL of TRIS buffer at pH=9. The resulting solution was spotted using a micropipette to place 5 μL spots on the rough side Biodyne B film and the film was allowed to air dry at room temperature for 30 minutes. Next 5 μL spots of alkaline phosphatase (Calbiochem) at concentrations of 3.5 units/mL or 1.7 units/mL were placed on the previously spotted film.

The average time to obtain a color response was 45 seconds for the 3.5 units/mL alkaline phosphatase and 20 seconds for the 1.7 units/mL alkaline phosphatase.

Example 3

Three solutions, A, B, and C, were prepared separately. Solution A was prepared by dissolving 25 mg of BCIP from Biosynth in 10 mL of deionized water. Solution B was prepared by dissolving 50 mg of NBT in 10 mL of deionized water. Solution C was prepared by adding 100 mg $MgCl_2$ and 100 mg $MnCl_2$ to 10 mL of the TRIS buffer prepared as described in Example 2. The solutions for Runs 1-10 were prepared by combining 400 μL of solution A with 100 μL of solution B and 500 μL of solution C. The solutions for Runs 11-20 were prepared by combining 800 μL of solution A with 100 μL solution B and 100 μL of solution C. The solutions for Runs 21-30 were prepared by combining 300 μL of solution A with 300 μL of solution B and 400 μL of solution C. Five microliters of each of the resulting solutions were placed in spots using a micropipette on Biodyne B film and allowed to air dry for 30 minutes at room temperature. In Runs 6-10, 16-20, and 26-30, the dried films were rinsed with flowing tap water and allowed to air dry once more for 30 minutes at room temperature. After drying for Runs 1-30, 5 μL of alkaline phosphatase (Calbiochem) solutions with concentrations of 3.5, 1.79, 0.89, 0.45, and 0.1 units/mL were each placed on the dried spots and the time needed to see the resulting grey-black color was recorded. The results that are shown in Table 1 were averaged for three spots.

TABLE 1

| Run Number | Concentration of alkaline phosphatase (units/mL) | Time until color developed (seconds) |
|---|---|---|
| 1 | 3.5 | 42 |
| 2 | 1.79 | 28 |
| 3 | 0.89 | 45 |
| 4 | 0.45 | 105 |
| 5 | 0.10 | 45 |
| 6 | 3.5 | 20 |
| 7 | 1.79 | 26 |
| 8 | 0.89 | 41 |
| 9 | 0.45 | 40 |
| 10 | 0.10 | 120 |
| 11 | 3.5 | 49 |
| 12 | 1.79 | 96 |
| 13 | 0.89 | 57 |
| 14 | 0.45 | 96 |
| 15 | 0.10 | 120(faint) |
| 16 | 3.5 | 46 |
| 17 | 1.79 | 39 |
| 18 | 0.89 | 50 |
| 19 | 0.45 | 99 |
| 20 | 0.10 | 154 |
| 21 | 3.5 | 20 |
| 22 | 1.79 | 29 |
| 23 | 0.89 | 26 |
| 24 | 0.45 | 59 |
| 25 | 0.10 | 90 |
| 26 | 3.5 | 26 |
| 27 | 1.79 | 26 |
| 28 | 0.89 | 39 |
| 29 | 0.45 | 109 |
| 30 | 0.10 | 60 |

The color developed in under 2 minutes regardless of rinsing with flowing tap water or changing the concentration of the BCIP. The concentration of the enzyme reached a limit of detection for Run 20.

Example 4

A 1× concentration of 50 μL BCI-gal/2 mL of iron buffer solution was prepared according to the manufacturer's instructions (Kirkegaard & Perry Laboratories, Inc.). A 2× concentration of 100 μL BCI-gal/2 mL of iron buffer solution was prepared. Next a 4× concentration of 100 μL BCI-gal/1 mL of iron buffer solution was prepared. Each of the solutions, 1×, 2×, and 4× were spotted on an Osmonics positively charged nylon membrane using a micropipette to place 10 μL drops and the film was allowed to air dry at room temperature for 30 minutes. Next 10 μL drops of β-galactosidase (supplied at 590 units/mL by (Sigma-Aldrich) in concentrations of 5.9, 0.59, 0.059, and 0.0059 units/spot or 0.5, 0.05, 0.005, 0.0005 mg/spot. The time needed for development of color was recorded in seconds. The results are shown in Table 2.

TABLE 2

| | β-galactosidase | | Time to color development for BCI-gal/iron buffer concentration | | |
|---|---|---|---|---|---|
| Run | concentration | | 1X | 2X | 4X |
| Number | (mg/spot) | (units/spot) | (seconds) | (seconds) | (seconds) |
| 1 | 0.5 | 5.9 | 10 | 10 | 7 |
| 2 | 0.05 | 0.59 | 30 | 30 | 17 |
| 3 | 0.005 | 0.059 | 43 | 37 | 25 |
| 4 | 0.0005 | 0.0059 | >120 | >120 | 120 (faint) |

Example 5

A solution of esculin (1 mg/mL)/FeCl$_3$ (1 mg/mL) was spotted on the rough side of Biodyne B film using a micropipette to place 5 µL drops and the film was allowed to air dry at room temperature for 30 minutes. Next 5 µL drops of β-glucosidase concentrations of 625, 312.5, 156.25, 78.125, and 39.0625 were placed on the esculin/FeCl$_3$ spots and the time needed for development of color was recorded. esculin worked well with pure enzyme systems. The results are shown in Table 3.

TABLE 3

| Run | β-glucosidase (units/mL) | Time for development of color (seconds) |
|---|---|---|
| 1 | 625.0000 | 5 |
| 2 | 312.5000 | 5 |
| 3 | 156.2500 | 10 |
| 4 | 78.1250 | 20 |
| 5 | 39.0625 | 20 |

Example 6

Test tubes were filled with 100 µL a solution of esculin (1 mg/mL)/FeCl$_3$ (1 mg/mL). Next 100 µL of β-glucosidase at concentrations of 5, 0.5, 0.25, 0.125, 0.0625, 0.05, 0.025, and 0.0025 units/mL were dropped into the test tubes containing the esculin/FeCl$_3$ solution and the time necessary for development of color change from green to black was recorded. The results are shown in Table 4.

TABLE 4

| Run | β-glucosidase (units/mL) | Time for development of color (seconds) |
|---|---|---|
| 1 | 5 | instant |
| 2 | 0.5 | 10 |
| 3 | 0.25 | 30 |
| 4 | 0.125 | 60 |
| 5 | 0.0625 | 120 |
| 6 | 0.05 | 150 |
| 7 | 0.025 | 300 |
| 8 | 0.0025 | 600 |
| Control | Pure water | No change |

Example 7

A solution of esculin (1 mg/mL)/FeCl$_3$ (1 mg/mL) was spotted on the rough side of Biodyne B film using a micropipette to place 5 µL drops and the film was allowed to air dry at room temperature for 30 minutes. Clinical endoscope soil samples (patient soil) were collected by flushing 10 mL of phosphate buffered saline through the biopsy lumen of a colon scope following a colonoscopy procedure at Mayo Clinic in Rochester, Minn. Then 100 µL of the clinical endoscope soil samples was placed on the esculin/FeCl$_3$ spots and the time necessary for development of color was recorded. Color development took longer than 10 minutes.

Example 8

Four samples of a Metricel SB-6407 membrane were spotted using a micropipette to place 10 µL of BCIP/NBT solution per spot. The spots were allowed to air dry at room temperature. One spotted membrane was respotted with 10 µL alkaline phosphatase (Sigma-Aldrich) solution (500 µg/mL alkaline phosphatase in distilled water) per spot. Two of the BCIP/NBT spotted membranes were respotted with 10 µL (per spot) of fluid samples obtained from a used gastrointestinal endoscope prior to manual cleaning and after manual cleaning respectively. The fourth BCIP/NBT spotted membrane was respotted with 10 µL distilled water per spot.

A blue-purple color due to product of the reaction of enzyme and indicator appeared within 2 minutes of addition of enzyme in both the pure sample and the pre-cleaning sample. The post-cleaning sample did not exhibit a visible colorimetric response within 2 minutes, nor did the spots treated with distilled water alone. The results are shown in Table 5.

TABLE 5

| Run | Treatment | Color Change within 2 minutes of addition of enzyme |
|---|---|---|
| 1 | Alkaline phosphatase solution | Colorless to blue-purple color |
| 2 | Samples from used gastrointestinal endoscope prior to manual cleaning | Colorless to blue-purple color |
| 3 | Samples from used gastrointestinal endoscope after manual cleaning | No color change |
| 4 | Distilled water | No color change |

Example 9

A HDPE TIPS membrane was made according to the process described in U.S. Pat. No. 4,539,256 (Example 23) except instead of extruding into a water quench bath, the extruded membrane was taken onto a chilled patterned casting wheel as described in U.S. Pat. No. 5,120,594.

Several HDPE TIPS membranes were fastened to a metal frame, coated by pouring a 2.5% EVOH in 60:40 IPA:water solution and spreading using a rubber spreader to smooth and remove excess. Coated membranes were allowed to dry at room temperature overnight. Six samples were coated by pouring 5:1, 2:1 and 1:1 solutions of poly(diallyldimethylammonium) chloride (PDAMAC) (<100,000 MW supplied in 40 wt % water) in deionized water and 5:1, 2:1 and 1:1 solutions of poly(diallyldimethylammonium) chloride (100,000-200,000 MW supplied in 20 wt % water) in deionized water and allowed to air dry at ambient temperature. The EVOH- and PDAMAC-coated membranes were spotted with 10 µL BCIP/NBT solution per spot as in Example 1 and allowed to dry. These spots then were respotted with 10 µL alkaline phosphatase (Sigma-Aldrich) solution per spot at a concentration of 500 µg/mL in distilled water.

A blue-purple colorimetric response was visible within 2 minutes on the PDAMAC-coated samples, but not on the samples coated with EVOH alone. On both of the PDAMAC-coated samples, the rate of the response was 5:1>2:1>1:1. The results are shown in Table 6.

TABLE 6

| Run | Coating | Treatment | Color Change | Time (minutes) |
|---|---|---|---|---|
| 1 | 2.5% EVOH in 60 IPA: 40 water | Alkaline phosphatase | No change | 2 |
| 2 | 5:1 EVOH:PDAMAC (<100K MW) | Alkaline phosphatase | Colorless to blue-purple | 2 |

TABLE 6-continued

| Run | Coating | Treatment | Color Change | Time (minutes) |
|---|---|---|---|---|
| 3 | 2:1 EVOH:PDAMAC (<100K MW) | Alkaline phosphatase | Colorless to blue-purple | 2 |
| 4 | 1:1 EVOH:PDAMAC (<100K MW) | Alkaline phosphatase | Colorless to blue-purple | 2 |
| 5 | 5:1 EVOH:PDAMAC (100-200K MW) | Alkaline phosphatase | Colorless to blue-purple | 2 |
| 6 | 2:1 EVOH:PDAMAC (100-200K MW) | Alkaline phosphatase | Colorless to blue-purple | 2 |
| 7 | 1:1 EVOH:PDAMAC (100-200K MW) | Alkaline phosphatase | Colorless to blue-purple | 2 |

Example 10

Using a micropipette approximately 5 microliters of BCIP/NBT solution per spot was placed onto Silica Gel Glass Backed TLC Plates (2.54 cm×7.62 cm). The spots were dried using warm air supplied by a Model #HG-751 heat gun (Master Appliance Corp., Racine, Wis.). One of the spotted glass plates was used as a control and was not placed in a water bath. The other spotted glass plates (test plates) were placed into a water bath (25° C.) for 2 minutes, removed, and dried again using the heat gun. Next 5 microliters of alkaline phosphatase (Sigma-Aldrich) solution (25 mg phosphatase/mL water) was placed on the indicator spots on the test plates and the control plate. For all enzyme indicator combinations, a purple color due to reacted indicator was noticeable within two minutes. Subsequently, for all colored spots on both control plate and test plates, the color was not washed away when they were placed into a water bath (25° C.). The results of this experiment indicated that spotted enzyme indicator remained bound to silica even after being washed with water and that it reacted with enzyme in its bound state. Additionally, the experiment demonstrated that reacted enzyme indicator remains bound to silica in the presence of water.

Example 11

Metricel SB-6407 membrane (comprising quaternary ammonium groups, available from Pall) was spotted as in Example 1 with BCIP/NBT, rinsed with flowing tap water, dried, and allowed to react with alkaline phosphatase (Sigma-Aldrich). A blue-purple color due to product of the reaction of enzyme and indicator appeared within 2 minutes of addition of enzyme and could not be washed away with water.

Comparative Example A

A TexWipe swab (Item # TX712A from Texwipe Co, Inc., Upper Saddle River, N.J.) was treated in the same manner as the Metricel membrane in Example 11. When the swab was washed with water as in Example 11, the indicator was washed away from the swab. Additionally, color resulting from reaction of indicator and enzyme on the TexWipe swabs was readily washed away when rinsed with flowing tap water.

Comparative Example B

A support consisting of an uncoated PP TIPS membrane was prepared by the following steps: securing the membrane in a hoop to avoid shrinkage during the drying step; loading membrane with 2 mL of X-glc solution at a concentration of 0.0003 g/mL in DMF; and drying the membrane for 20 min at 58° C. The membrane was then tested for a calorimetric response by placing spots of 10 μl pure β-glucosidase solution at a concentration 100 units/mL on the loaded membrane using a micropipette and recording the time necessary for development of color. The aqueous enzyme solution did not wet the membrane when it was spotted onto the surface. No response was observed.

Example 12

A HDPE TIPS membrane was coated by dispensing and evenly spreading approximately 1 mL of EVAL solution (2.8% (w/w) EVAL in 60:40 isopropyl alcohol:water) using a plastic pipette. The coated membrane was further prepared by the following steps: securing the membrane in a 10.08 cm in diameter hoop to avoid shrinkage during the drying step; loading membrane with 2 mL of X-glc solution at a concentration of 0.15 g/mL; and drying the membrane for 20 min at 58° C. in an incubator (Precision Mechanical Convection Incubator from GCA Corporation, Andover, Mass.).

The membrane was then tested at room temperature for colorimetric response by using a micropipette to place 10 μL of β-glucosidase solution in spots at concentrations of 100, 50, 25, 12.5, 6.3 and 3.1 units/mL in reagent-grade water on the loaded membrane and recording the time necessary for development of the color. In Run 6, when the color did not develop after 50 minutes at room temperature, the membrane including Runs 1-6 was heated to 58° C. in an incubator for 10 minutes. Then the membrane was removed from the incubator and allowed to cool to room temperature. The color continued to develop in the examples overnight at room temperature. Results are shown in Table 7.

TABLE 7

| Run Number | β-glucosidase dilutions (units/mL) | Time (minutes) |
|---|---|---|
| 1 | 100 | 1.5 |
| 2 | 50 | 2 |
| 3 | 25 | 2.5 |
| 4 | 12.5 | 5.0 |
| 5 | 6.3 | 6.0 |
| 6 | 3.1 | 10[1] |

[1]After 50 minutes at room temperature and 10 minutes at 58° C. in an incubator.

Example 13

A rayon/PP nonwoven support was prepared by the following steps: securing the nonwoven in a hoop to avoid shrinkage during the drying step; loading the nonwoven support with 2.5 mL of X-glc solution at a concentration of 0.15 g/mL in DMF; and drying the membrane for 20 min at 58° C. The X-glc loaded nonwoven support was then tested at room temperature for calorimetric response by using a micropipette to place 10 μL of β-glucosidase solution in spots at concentrations of 100, 50, 25, 12.5, 6.3 and 3.1 units/mL in regent-grade water on the loaded support and recording the time necessary for development of the color. In Run 6, when the color did not develop after 21 minutes at room temperature, the membrane including Runs 1-6 was heated to 58° C. in an incubator for 10 minutes. Then the membrane was removed from the incubator and allowed to cool to room temperature. Color continued to develop overnight. The contrast between the colorimetric response and the textured background made the detection of color more obvious sooner than on the TIPS membrane support in Example 12. Results are shown in Table 8.

TABLE 8

| Run Number | β-glucosidase dilutions (units/mL) | Time (minutes) |
|---|---|---|
| 1 | 100 | 1.0 |
| 2 | 50 | 1.5 |
| 3 | 25 | 2.0 |
| 4 | 12.5 | 3.0 |
| 5 | 6.3 | 4.0 |
| 6 | 3.1 | 10[1] |

[1]After 21 minutes at room temperature and 10 minutes at 58° C. in an incubator.

Example 14

A HDPE TIPS membrane support was prepared by the following steps: securing the membrane in a hoop to avoid shrinkage during the drying step; spotting the membrane with EVAL solution at 2.8% (w/w) EVAL in 60:40 isopropyl alcohol:water using a plastic pipette SAMCO Transfer Pipettes, San Fernando, Calif.); air drying the spotted membrane overnight at 25° C.; loading the spots on membrane with 2 mL of X-glc chemistry at a concentration of 0.22 g/mL in DMF; and drying the spotted membrane for 20 min at 58° C. The membrane was wettable by the aqueous enzyme solutions only where EVAL was spotted onto the surface.

The membrane was then tested for calorimetric response by using a micropipette to place 10 μL of β-glucosidase solution onto the EVAL/X-glc spots at concentrations of 100, 50, 25, 12.5, 6.3 and 3.1 units/mL in reagent-grade water on the loaded membrane and recording the time necessary for development of color. Color continued to develop overnight. The colors were more vibrant than with the EVAL-coated HDPE (Example 12) because the sample was confined to a specific area, but the response did not develop and faster. Results are shown in Table 9.

TABLE 9

| Run Number | β-glucosidase dilutions (units/mL) | Time (minutes) |
|---|---|---|
| 1 | 100 | 1.5 |
| 2 | 50 | 3.0 |
| 3 | 25 | 4.0 |
| 4 | 12.5 | 5.5 |
| 5 | 6.3 | 7.0 |
| 6 | 3.1 | 12.0 |

Example 15

A HDPE TIPS membrane support was prepared by the following steps: securing the membrane in a hoop to avoid shrinkage during the drying step; spotting the membrane with EVAL solution at 2.8% (w/w) EVAL in 60:40 isopropyl alcohol:water using a plastic pipette; drying the spotted membrane overnight at 25° C.; loading some of the hydrophilic spots on membrane with 25 μL of X-glc at a concentration of 0.15 g/mL in DMF or with 25 μL of X-gal (Biosynth AG, Inc.) at a concentration of 0.15 g/mL in DMF; drying the spotted membrane for 5 min at 58° C.; loading other hydrophilic spots on the membrane with 25 μL of Coomassie Plus™ Protein Assay Reagent; and drying for 20 minutes at 58° C.

The spotted membrane was then tested for colorimetric response by using a micropipette to place 20 μl of β-glucosidase (sigma-Aldrich) in reagent-grade water or 20 μl of β-galactosidase (Worthington Biochemical Corp.) in reagent-grade water onto the EVAL/X-glc or EVAL/X-gal spots, respectively, with a concentration of 100 units/mL, and recording the time necessary for development of color.

Additionally *Pseudomonas aeruginosa* MBL 0484 from Microbiologics was grown overnight (16 hours) at 37° C. in tryptic soy broth (Becton Dickinson and Company, Sparks, Md.) and was used to test the spotted membrane for a colorimetric response. A micropipette was used to place 20 μL of serial 1:10 dilutions of *Pseudomonas aeruginosa* ($10^8$ CFU/mL) in calf serum on each type of indicator-loaded hydrophilic spot.

The enzyme, β-glucosidase in reagent-grade water, produced a response within 1.5 minutes for the X-glc chemistry. While the enzyme, β-galactosidase in reagent-grade water produced a blue response within 1 minute for the X-gal chemistry. The Coomassie chemistry produced a response within 20 seconds for every dilution of *Pseudomonas aeruginosa* culture. The $10^8$ CFU/mL *Pseudomonas aeruginosa* culture did not produce a response for the X-gal or X-glc chemistries.

Example 16

A HDPE TIPS membrane support was prepared by the following steps: securing the membrane in a hoop to avoid shrinkage during the drying step; spotting the membrane with EVAL solution at 2.8% (w/w) EVAL in 60:40 isopropyl alcohol:water using a plastic pipette; drying the spotted membrane overnight at 25° C.; loading six hydrophilic spots on membrane with 20 μL of a combination of X-glc, X-gal (Biosynth AG, Inc.), and X-phos-p-tol chemistries at a concentration of 0.07 g/mL of each in DMF; loading another six hydrophilic spots on the membrane with 20 μl of a combination of Magenta™-glc, Magenta™-gal, and Magenta™-phos-p-tol chemistries at a concentration of 0.06 g/mL of each in DMF; and drying for 20 minutes at 58° C.

The membrane was then tested for calorimetric response by using a micropipette to place 20 μL of β-glucosidase (Sigma-Aldrich) in reagent-grade water (100 units/mL), 20 μL of β-galactosidase (Worthington Biochemical Corp.) in reagent-grade water (100 units/mL), and 20 μL of calf serum, 20 μL clinical endoscope soil samples (Mayo Clinic, Rochester, Minn.) for each type of coated hydrophilic spot on the loaded membrane and recording the time necessary for development of color. Clinical endoscope soil samples (patient soil) were collected by flushing 10 mL of phosphate buffered saline through the biopsy lumen of a colonoscope following colonoscopy procedure and following the cleaning procedure for the scope.

The β-glucosidase reacted within 1 minute on the Magenta™ combination and within 2 minutes on the X-chemistries combination. β-galactosidase reacted within 2 minutes for each of the X-chemistry combinations and Magenta™ chemistry combinations. The calf serum did not react within 10 minutes. The PB78 clinical sample from Mayo reacted within 4 minutes for the Magenta™-glc, Magenta™-gal, or Magenta™-phos-p-tol chemistry combination and within 6 minutes for the X-glc, X-gal, or X-phos-p-tol chemistry combination.

Example 17

A HDPE TIPS membrane support was placed in a hoop, spotted with EVAL solution and allowed to dry as described in Example 15. The spotted membrane was subsequently coated with a 1.5 mL of 1:1000 of ω-saccharinamidoundecyltrichlorosilane in hexadecane, allowed to react for 20 minutes, washed with MEK and allowed to air dry three times. After drying, the hydrophilic spots on the treated membrane were spotted with 20 µL of a combination of X-glc, X-gal (Biosynth AG, Inc.), and X-phos-p-tol chemistries in DMF at a concentration of 0.2 g total substrate/mL (0.07 g X-chemistry/mL for each chemistry) and allowed to react for approximately 20 minutes. A PBS Buffer, pH 7.4 was prepared by combining 0.14 M NaCl (EM Science, Gibbstown, N.J.) 0.006 M $K_2HPO_4$ (Sigma-Aldrich) and 0.02 M $KH_2PO_4$ (Sigma-Aldrich). The treated membrane was washed twice with the PBS Buffer and with 1% Tween™ 80 and allowed to air dry.

The hydrophilic spots on the membrane were then tested for calorimetric response with 20 µL of β-glucosidase (Sigma-Aldrich), β-galactosidase (Worthington Biochemical Corp.), calf serum, and clinical endoscope soil samples prepared as in Example 16 and the time needed for development of color was recorded. The time needed to develop a color was not within a 2-minute time interval, but color did develop within two hours for β-glucosidase, β-galactosidase, and one soiled endoscope sample with the combination of X-gal, X-glc, and X-phos.

Example 18

A HDPE TIPS membrane support was prepared by securing the membrane in hoop to avoid shrinkage during the drying step, coating the membrane with EVAL as described in Example 12, loading the coated membrane with 2 mL of 4-MU-β-D-glc chemistry at a concentration of 0.0003 g/mL, and drying for 20 min at 58° C.

The membrane was then tested for fluorescent response by spotting the loaded membrane with 10 µL of pure β-glucosidase (Sigma-Aldrich) solution and at 50, 25, 12.5, 6.3, and 3.1 units/mL dilutions in reagent grade water, exposing the membrane to UV light (365 nm) until a fluorescent response developed and recording the time. The results are shown in Table 10.

TABLE 10

| Run Number | β-glucosidase dilutions (units/mL) | Time (seconds) |
|---|---|---|
| 1 | 100 | instant |
| 2 | 50 | 20 |
| 3 | 25 | 30 |
| 4 | 12.5 | 30 |
| 5 | 6.3 | 45 |
| 6 | 3.1 | 85 |

Example 19

A rayon/PP nonwoven support was prepared by securing the nonwoven in a hoop to avoid shrinkage during the drying step, coating the nonwoven with 3 mL of 4-MU-β-D-glc chemistry at a concentration of 0.0003 g/mL in DMF, and drying for 20 min at 58° C. The membrane was then tested for fluorescent response by spotting the loaded membrane with 10 µL if pure β-glucosidase (Sigma-Aldrich) solution and at 50, 25, 12.5, 6.3, and 3.1 units/mL dilutions in reagent grade water, exposing the membrane to UV light (365 nm) until a fluorescent response developed and recording the time. The results are shown in Table 11.

TABLE 11

| Run Number | β-glucosidase dilutions (units/mL) | Time (seconds) |
|---|---|---|
| 1 | 100 | instant |
| 2 | 50 | 20 |
| 3 | 25 | 30 |
| 4 | 12.5 | 30 |
| 5 | 6.3 | 60 |
| 6 | 3.1 | 90 |

Example 20

A HDPE TIPS membrane support was placed in a hoop, coated with EVAL solution as described in Example 18 subsequently coated with 1.5 mL of 1:1000 ω-saccharinamidoundecyltrichlorosilane in hexadecane, allowed to react for 20 minutes, washed with MEK and allowed to air dry three times. After drying, the treated membrane was coated with 20 µL of a solution of 4-MU-β-D-glc chemistry at a concentration of 0.0003 g/mL in DMF, washed twice with the PBS Buffer, pH 7.4, prepared as described in Example 17 and with 1% Tween™ T 80 and allowed to air dry.

The coated membrane was then tested for fluorescent response by placing 10 µL of β-glucosidase (Sigma-Aldrich) in spots using a micropipette on the membrane, exposing the membrane to UV light (365 nm) until a fluorescent response developed and recording the time. The fluorescence response for enzyme solution at 100 units/mL was instantaneous.

Example 21

A GHP-450 membrane support was prepared by securing the membrane in a hoop to avoid shrinkage during the drying step, coating the membrane with 3 mL of 4-MU-β-D-glc chemistry at a concentration of 0.0003 g/mL in DMF, and drying for 20 min at 58° C. The membrane was then tested as then tested for fluorescent response by spotting the loaded membrane with 10 µL of pure β-glucosidase (Sigma-Aldrich) solution and at 50, 25, 12.5, 6.3, and 3.1 units/mL dilutions in reagent grade water, exposing the membrane to UV light (365 nm) until a fluorescent response developed and recording the time. The results are shown in Table 12.

TABLE 12

| Run Number | β-glucosidase dilutions (units/mL) | Time (seconds) |
|---|---|---|
| 1 | 100 | instant |
| 2 | 50 | instant |
| 3 | 25 | instant |
| 4 | 12.5 | 60 |
| 5 | 6.3 | 90 |
| 6 | 3.1 | 120 |

Example 22

A HDPE TIPS membrane support was prepared by securing the membrane in a hoop to avoid shrinkage during the drying step, coating the membrane with EVAL as described in Example 12, subsequently coating with 2 mL of OPA solution at a concentration of 0.8 mg/mL, and drying for 30 min at 58° C. The membrane was then tested for fluorescent response by spotting the loaded membrane with 10 µL of BSA solution at 2, 1, 0.5, 0.25, 0.13 and 0.06 mg/mL in reagent grade water, exposing the membrane to UV light (365 nm) until a fluorescent response developed and recording the time. The results are shown in Table 13.

TABLE 13

| Run Number | BSA dilutions (mg/mL) | Time (minutes) |
|---|---|---|
| 1 | 2 | 1 |
| 2 | 1 | 1.5 |
| 3 | 0.5 | 3.5 |
| 4 | 0.25 | 5 |
| 5 | 0.13 | >10[1] |
| 6 | 0.06 | >10[1] |

[1]No response was observed within 10 minutes.

Example 23

A rayon/PP nonwoven support was prepared by securing the nonwoven in a hoop to avoid shrinkage during the drying step, loading the membrane with 3 mL of OPA solution at a concentration of 0.8 mg/mL, and drying for 30 min at 58° C. The nonwoven support was then tested for fluorescent response by spotting the loaded membrane using a micropipette with 10 µL of BSA solution at 2, 1, 0.5, 0.25, 0.13 and 0.06 mg/mL in reagent-grade water, exposing the membrane to UV light (365 nm) until a fluorescent response developed and recording the time. The results are shown in Table 14.

TABLE 14

| Run Number | BSA dilutions (mg/mL) | Time (minutes) |
|---|---|---|
| 1 | 2 | 1 |
| 2 | 1 | 2.5 |
| 3 | 0.5 | >10[1] |
| 4 | 0.25 | >10[1] |
| 5 | 0.13 | >10[1] |
| 6 | 0.06 | >10[1] |

[1]No response was observed within 10 minutes.

Example 24

Two solutions were prepared by first dissolving 25 mg of 5-bromo-6-chloro-3-indolyl phosphate, disodium salt in 10 mL of deionized water and then dissolving 50 mg of NBT was dissolved 10 mL of deionized water. Next four 10 mL TRIS buffer solutions (A, B, C, D) were prepared as described in Example 2. To Buffer Solution A, 250 mg of MnCl$_2$ was added. To Buffer solution B, 250 mg of MgCl$_2$ was added. To Buffer solution C, 250 mg of MgCl$_2$ and 250 mg of MnCl$_2$ were added. Buffer solution D had no metal salt additions. Four 5-bromo-6-chloro-3-indolyl phosphate, disodium salt/NBT/Buffer solutions were prepared by combining 400 µL of 5-bromo-6-chloro-3-indolyl phosphate, disodium salt/water solution, 100 µL NBT/water solution, and 500 µL of Buffer solution A, B, C, or D. The resulting four indicator solutions were labeled indicator solution 1, 2, 3, and 4 respectively. Five microliters of each of the four solutions was placed in spots on a Biodyne B film using a micropipette. The spots were allowed to air dry for 30 minutes at room temperature. Each spot was respotted with 5 microliters of alkaline phosphatase (Calbiochem) at a concentration of 1.79 units/mL. The time needed to develop color, the initial indicator spot color on the film, and the color of the indicator spot after ageing at ambient temperature and light conditions for 1 day and for 1 week were recorded.

The samples containing MnCl$_2$ and MgCl$_2$ showed shortened times for color development with the alkaline phosphatase enzyme. Samples with MgCl$_2$ alone resulted in a spotty color that aged in the same manner as Indicator Solution 4 (containing neither MnCl$_2$ nor MgCl$_2$). The yellow color of manganese salt-containing spots gave a good contrast between the unreacted indicator and that of the brown-black color of the reacted indicator. Results are shown in Table 15.

TABLE 15

| Indicator Solution Number | Time to develop color (seconds) | Initial indicator spot color | Indicator spot color after 1 day | Indicator spot color after 1 week |
|---|---|---|---|---|
| 1 | 40 | Yellow | Yellow | Yellow |
| 2 | 17 | Colorless | Purple | Purple |
| 3 | 30 | Yellow | Yellow | Yellow |
| 4 | 110 | Colorless | Purple | Purple |

Example 25

A HDPE TIPS membrane support was placed in a hoop, spotted with EVAL solution and allowed to dry as described in Example 15. Then each hydrophilic spot on the membrane was loaded with 10 µL of X-gal solution prepared by combining 200 µL of X-gal (Kirkegaard & Perry Laboratories, Inc.) with 1 mL iron buffer; 10 µL BCIP/NBT (3-Part Phosphatase Substrate System from Kirkegaard & Perry Laboratories, Inc.) prepared by combining 4 mL of BCIP, 1 mL of NBT, and 5 mL of TRIS buffer; 10 µL of 4-MU-β-D-gal prepared by combining 0.3 g/L of water and autoclaving for 15 minutes at 121° C.; 10 µL of 4-MU-β-D-glc prepared by combining 0.3 g/L of water and autoclaving for 15 minutes at 121° C.; or 10 µL of 4-MU-phos prepared by dissolving 0.03 g in 100 microliters DMF and diluting with 100 mL of water. The solutions were placed on the membrane using a micropipette and allowed to air dry at room temperature.

The membrane was then tested for colorimetric response by using a micropipette to place 10 µL of β-galactosidase (Sigma) in reagent-grade water at concentrations of 188, 18.8, 9.4, and 1.88 units/mL, 10 µL of β-glucosidase (Worthington Biochemical Corp.) in reagent-grade water at concentrations 50, 5, 2.5 an 0.5 units/mL, or 10 µL alkaline phosphatase (Calbiochem) in reagent-grade water at concentrations of 3582, 358, 35.8, 3.58, 0.358 units/mL for each type of coated hydrophilic spot on the loaded membrane and recording the time necessary for development of color. The results are shown in Table 16.

TABLE 16

| Run Number | Indicator Chemistry | Enzyme tested | Enzyme concentration (units/mL) | Time to develop color (seconds) |
|---|---|---|---|---|
| 1 | BCIP/NBT | alkaline phosphatase | 358 | 10 |
| 2 | BCIP/NBT | alkaline phosphatase | 35.8 | 20 |
| 3 | BCIP/NBT | alkaline phosphatase | 3.58 | 30 |
| 4 | BCIP/NBT | alkaline phosphatase | 0.358 | 90 |
| Control A | BCIP/NBT | water | 0 | No Change |
| 5 | X-gal | β-galactosidase | 188 | 45 |
| 6 | X-gal | β-galactosidase | 18.8 | 60 |
| 7 | X-gal | β-galactosidase | 9.4 | 105 |
| 8 | X-gal | β-galactosidase | 1.88 | 180 |
| 9 | MU-gal | β-galactosidase | 188 | instant |

TABLE 16-continued

| Run Number | Indicator Chemistry | Enzyme tested | Enzyme concentration (units/mL) | Time to develop color (seconds) |
|---|---|---|---|---|
| 10 | MU-gal | β-galactosidase | 18.8 | 10 |
| 11 | MU-gal | β-galactosidase | 9.4 | 15 |
| 12 | MU-gal | β-galactosidase | 1.88 | 30 |
| 13 | 4-MU-β-D-glc | β-galactosidase | 50 | instant |
| 14 | 4-MU-β-D-glc | β-galactosidase | 5 | 5 |
| 15 | 4-MU-β-D-glc | β-galactosidase | 2.5 | 5 |
| 16 | 4-MU-β-D-glc | β-galactosidase | 0.5 | 10 |
| 17 | MU-phos | alkaline phosphatase | 3582 | instant |
| 18 | MU-phos | alkaline phosphatase | 358 | 10 |
| 19 | MU-phos | alkaline phosphatase | 35.8 | 15 |
| 20 | MU-phos | alkaline phosphatase | 3.58 | 60 |
| 21 | MU-phos | alkaline phosphatase | 0.358 | 105 |
| Control B | MU-phos | water | 0 | No Change |

Example 26

A HDPE TIPS membrane support was prepared by securing the membrane in a hoop to avoid shrinkage during the drying step, coating the membrane with EVAL as described in Example 12, subsequently placing 6 drops of 10 μL BCIP/NBT (3-Part Phosphatase Substrate System from Kirkegaard & Perry Laboratories, Inc.) prepared by combining 4 mL of BCIP, 1 mL of NBT, and 5 mL of TRIS buffer in spots using a micro pipette and allowing to air dry at room temperature.

The membrane was then tested for calorimetric response by using a micropipette to place 10 μL of alkaline phosphatase (Calbiochem) in reagent-grade water at concentrations of 3582, 358, 3.58, 0.358 units/mL on the 5 spots of BCIP/NBT. The sixth BCIP/NBT spot was tested in the same manner with 10 μL of water. The time necessary for development of color was recorded. The results are shown in Table 17

TABLE 17

| Run Number | Enzyme tested | Enzyme concentration (units/mL) | Time to develop color (seconds) |
|---|---|---|---|
| 1 | alkaline phosphatase | 3582 | 5 |
| 2 | alkaline phosphatase | 358 | 15 |
| 3 | alkaline phosphatase | 35.8 | 25 |
| 4 | alkaline phosphatase | 3.58 | 30 |
| 5 | alkaline phosphatase | 0.358 | 70 |
| 6 | Water (no enzyme) | 0 | No Change |

Example 27

By first dissolving 5 mg of 5-bromo-6-chloro-3-indolyl phosphate, disodium salt in 10 mL deionized water and then dissolving 50 mg of NBT in 10 mL deionized water, two solutions were prepared. Next a 10 mL TRIS buffer solution was prepared as described in Example 2 and 100 mg of $MnCl_2$ and 100 mg of MgCl2 were added. Then, 300 microliters of the 5-bromo-6-chloro-3-indolyl phosphate solution and 300 microliters of the NBT solution were combined with 400 microliters of the TRIS buffer solution containing $MgCl_2$ and $MnCl_2$. Five microliters of the indicator solution was used to place thirty spots (1 mm diameter and 1 mm apart) onto a piece of a Biodyne B film (1 cm×3 cm) using a micropipette. A polyethylene tube simulating the inside of the biopsy channel of an endoscope was filled with 2 mL of contents flushed from a patient soiled endoscope and then emptied. Within 10 seconds the spotted Biodyne B film was pushed through the lumen of the soiled polyethylene tube. A colorimetric reaction occurred within 20 seconds, thus indicating the presence of alkaline phosphatase in the polyethylene lumen that had been soiled with the patient soiled endoscope contents.

Example 28

Several 70% rayon/30% polyester nonwoven supports were treated with three amine-containing silanes: (N-trimethoxysilylpropyl)polyethyleneimine, 3-aminopropyltriethoxysilane, and N-trimethoxysilylpropyl-N,N,N-trimethylammonium chloride; and a wetting agent, 3-glycidoxypropyltrimethoxysilane (GPS) by dip coating. First a slightly acidic solution of 95 percent water/5 percent ethanol was prepared by adding sulfuric acid drop wise to obtain pH=4. GPS and each aminosilane were added to the acidic solution in a ratio May 5, 1990, respectively. After the nonwoven was dipped in one of the aminosilane solutions, it was dipped into two sequential ethanol baths and heat cured at 70° C. for 1½ to 2 hours in an oven (Commercially available as Model LFD1-42-3 from Despatch, Lakeville, Minn.). For comparison to the amine-containing nonwovens, one sample of the nonwoven was left untreated and one sample was only treated with GPS (no amine groups present).

A micropipette was used to place several 5-microliter spots of NBT/BCIP 1-Step™ Solution onto each of the three aminosilane-treated samples, the untreated sample and the GPS-treated sample. These spots were allowed to air dry at room temperature for at least 30 minutes. Next, 5 microliters of alkaline phosphatase (Calbiochem) at concentrations of 3.5, 1.75, 0.35, and 0.175 units/mL were placed onto the dried spots of NBT/BCIP on the nonwoven support using a micropipette. For comparison, 5 microliters of sterile, ultra-pure water (0 units/μL of the enzyme) were also placed on additional dried spots of NBT/BCIP using a micropipette. The time needed for the first appearance of color was recorded and the results are shown in Table 18.

To determine if the background color of the unreacted NBT/BCIP 1-Step™ Solution changed over time, some of the unreacted dried spots of NBT/BCIP on the nonwoven support were observed for the initial color and the color change after 1 day. These observations are shown in Table 19.

TABLE 18

| Run Number | Treated with Aminosilanes and GPS | Enzyme-alkaline phosphatase (units/mL) | Time to develop color (seconds) |
|---|---|---|---|
| 1 | None (Untreated) | 0 (Water only) | No Change[1] |
| 2 | None (Untreated) | 0.175 | 150 |
| 3 | None (Untreated) | 0.350 | 90 |
| 4 | None (Untreated) | 1.75 | 55 |
| 5 | None (Untreated) | 3.50 | 30 |
| 6 | (N-trimethoxysilylpropyl) polyethyleneimine | 0 (Water only) | No Change[1] |
| 7 | (N-trimethoxysilylpropyl) polyethyleneimine | 0.175 | 45 |
| 8 | (N-trimethoxysilylpropyl) polyethyleneimine | 0.350 | 41 |
| 9 | (N-trimethoxysilylpropyl) polyethyleneimine | 1.75 | 30[2] |

TABLE 18-continued

| Run Number | Treated with Aminosilanes and GPS | Enzyme-alkaline phosphatase (units/mL) | Time to develop color (seconds) |
|---|---|---|---|
| 10 | (N-trimethoxysilylpropyl) polyethyleneimine | 3.50 | 20[2] |
| 11 | 3-aminopropyltriethoxysilane | 0 (Water only) | No Change[1] |
| 12 | 3-aminopropyltriethoxysilane | 1.75 | 6[3] |
| 13 | 3-aminopropyltriethoxysilane | 3.50 | 7[3] |
| 14 | N-trimethoxysilylpropyl-N,N,N-trimethylammonium chloride | 0 (Water only) | No Change[1] |
| 15 | N-trimethoxysilylpropyl-N,N,N-trimethylammonium chloride | 0.175 | 35 |
| 16 | N-trimethoxysilylpropyl-N,N,N-trimethylammonium chloride | 0.350 | 25 |
| 17 | N-trimethoxysilylpropyl-N,N,N-trimethylammonium chloride | 1.75 | 13[3] |
| 18 | N-trimethoxysilylpropyl-N,N,N-trimethylammonium chloride | 3.50 | 13[3] |
| 19 | GPS only | 0 (Water only) | No Change[1] |
| 20 | GPS only | 1.75 | 8 |
| 21 | GPS only | 3.50 | 9 |

[1]No change within 10 minutes
[2]Colors darken overnight
[3]Colors stable after 1 week.

TABLE 19

| Observation Run Number | Treated with Aminosilanes and GPS | Initial Indicator Spot Color | Color of Indicator Spot after 1 day |
|---|---|---|---|
| 22 | Untreated | Colorless | Faint purple |
| 23 | N-trimethoxysilylpropyl-N,N,N-trimethylammonium chloride | Colorless | Faint purple |
| 24 | (N-trimethoxysilylpropyl) polyethyleneimine | Colorless | Purple |

Example 29

Several 70% rayon/30% polyester nonwoven supports were treated with one of three amine-containing silanes: (N-trimethoxysilylpropyl)polyethyleneimine, 3-aminopropyltriethoxysilane, and N-trimethoxysilylpropyl-N,N,N-trimethylammonium chloride; and a wetting agent, 3-glycidoxypropyltrimethoxysilane (GPS) as described for Example 28. Additionally, one sample of the nonwoven was left untreated. Three solutions, labeled solution A, solution B, and solution C, were prepared in a similar manner to the solutions described in Examples 3 and 24. Solution A was prepared by combining 25 mg of BCIP with 10 mL deionized water. Solution B was prepared by dissolving 15 mg NBT in 10 mL deionized water. Solution C was prepared by combining 250 mg each $MnCl_2$ and $MgCl_2$ and dissolving in 10 mL of TRIS buffer (pH=8.9). The TRIS buffer was prepared according to the description for Example 2. The indicator solution was prepared by combining 400 microliters of solution A, 100 microliters of solution B, and 500 microliters of solution C, yielding a ratio of 4:1:5 BCIP:NBT:TRIS buffer with $MnCl_2$ and $MgCl_2$ salts. A micropipette was used to place several 5-microliter drops of the 4:1:5 indicator solution in a spotted pattern onto each of the three aminosilane treated samples and an untreated sample. These spots were allowed to air dry at room temperature for at least 30 minutes. Next, 5 microliters of alkaline phosphatase (Calbiochem) at concentrations of 1.00, 0.50, 0.10, 0.05, and 0.01 units/mL were placed onto the dried spots of indicator solution using a micropipette. For comparison, 5 microliters of deionized water (0 units/mL of the enzyme) were also placed on additional dried spots of indicator solution using a micropipette. The time needed for the first appearance of the characteristic purple-black color was recorded and the results are shown in Table 20.

To determine if the background color of the unreacted 4:1:5 BCIP:NBT:TRIS buffer and $MnCl_2$ and $MgCl_2$ salts changed over time, some of the unreacted dried spots on the nonwoven support were observed for the initial color and the color change after 1 day (dry). Additionally to determine the stability of the indicator color, both reacted and unreacted dried samples were immersed in water for 1 day (wet) and for 1 week (wet) and observed for color change. Samples treated with (N-trimethoxysilylpropyl) polyethyleneimine and N-trimethoxysilylpropyl-N,N,N-trimethylammonium chloride showed a stable color using the BCIP/NBT/TRIS solution before and after reaction with the enzyme. Results are shown in Table 21.

TABLE 20

| Run Number | Treated with Aminosilanes and GPS | Enzyme-alkaline phosphatase (units/mL) | Time to develop color (seconds) |
|---|---|---|---|
| 1 | None (Untreated) | 0 (Water only) | No Change[1] |
| 2 | None (Untreated) | 0.01 | No Change[1] |
| 3 | None (Untreated) | 0.05 | No Change[1] |
| 4 | None (Untreated) | 0.10 | 240 |
| 5 | None (Untreated) | 0.50 | 110 |
| 6 | None (Untreated) | 1.00 | 90 |
| 6 | (N-trimethoxysilylpropyl) polyethyleneimine | 0 (Water only) | No Change[1] |
| 7 | (N-trimethoxysilylpropyl) polyethyleneimine | 0.01 | No Change[1] |
| 8 | (N-trimethoxysilylpropyl) polyethyleneimine | 0.05 | 240 |
| 9 | (N-trimethoxysilylpropyl) polyethyleneimine | 0.10 | 80 |
| 10 | (N-trimethoxysilylpropyl) polyethyleneimine | 0.50 | 25 |
| 11 | (N-trimethoxysilylpropyl) polyethyleneimine | 1.00 | 10 |
| 12 | 3-aminopropyltriethoxysilane | 0 (Water only) | No Change[1] |
| 13 | 3-aminopropyltriethoxysilane | 0.01 | No Change[1] |
| 14 | 3-aminopropyltriethoxysilane | 0.05 | No Change[1] |
| 15 | 3-aminopropyltriethoxysilane | 0.10 | 90 |
| 16 | 3-aminopropyltriethoxysilane | 0.50 | 45 |
| 17 | 3-aminopropyltriethoxysilane | 1.00 | 25 |
| 18 | N-trimethoxysilylpropyl-N,N,N-trimethylammonium chloride | 0 (Water only) | No Change[1] |
| 19 | N-trimethoxysilylpropyl-N,N,N-trimethylammonium chloride | 0.01 | No Change[1] |
| 20 | N-trimethoxysilylpropyl-N,N,N-trimethylammonium chloride | 0.05 | 240 |
| 21 | N-trimethoxysilylpropyl-N,N,N-trimethylammonium chloride | 0.10 | 90 |
| 22 | N-trimethoxysilylpropyl-N,N,N-trimethylammonium chloride | 0.50 | 30 |
| 23 | N-trimethoxysilylpropyl-N,N,N-trimethylammonium chloride | 1.00 | 16 |

[1]No change within 10 minutes

TABLE 21

| Observation Run Number | Treated with Aminosilanes and GPS | Initial Indicator Spot Color | Color of Indicator Spot after 1 day | Color of Indicator Spot after 1 day (wet) | Color of Indicator Spot after 1 week (wet) |
|---|---|---|---|---|---|
| 24 | Untreated | Yellow | Yellow | Yellow | Colorless |
| 25 | N-trimethoxysilylpropyl-N,N,N-trimethylammonium chloride | Yellow | Yellow | Yellow | Yellow |
| 26 | (N-trimethoxysilylpropyl)polyethyleneimine | Yellow | Yellow | Yellow | Yellow |
| 27 | None (Untreated) | Purple | Purple | Light Purple | Very faint Purple |
| 28 | N-trimethoxysilylpropyl-N,N,N-trimethylammonium chloride | Purple | Purple | Purple | Purple |
| 29 | (N-trimethoxysilylpropyl)polyethyleneimine | Purple | Purple | Purple | Purple |

Example 30

Several 70% rayon/30% polyester nonwoven supports were treated with one of two amine-containing silanes: (N-trimethoxysilylpropyl)polyethyleneimine and N-trimethoxysilylpropyl-N,N,N-trimethylammonium chloride; and a wetting agent, 3-glycidoxypropyltrimethoxysilane (GPS) as described for Example 28. Additionally, one sample of the nonwoven was left untreated. A micropipette was used to place several 5-microliter drops in a spotted pattern of the 4:1:5 indicator solution prepared as described for Example 29 onto each of the two aminosilane treated samples and an untreated sample. These spots were allowed to air dry at room temperature for at least 30 minutes. Six (two per treated and untreated) dried samples were used to wipe up a 10-microliter drop of alkaline phosphatase (Calbiochem) (1 unit/milliliter) on a 2.54 cm by 7.62 cm (1 inches by 3 inches) glass slide. Another six (two per treated and untreated) dried samples were dipped into ultrapure water until thoroughly wet and used to wipe up a 20-microliter drop of alkaline phosphatase (3.5 units/milliliter) on a 2.54 cm by 7.62 cm (1 inch by 3 inches) glass slide. The time needed for the first appearance of the characteristic purple-black color was recorded. Aminosilane-treated nonwovens exhibited a color change when used either dry or wet, and the shape of the original indicating drop was maintained. The control samples showed smearing of the indicator chemistry after the reaction with the enzyme. Results are shown in Table 22.

TABLE 22

| Run Number | Treated with Aminosilane and GPS | Time to develop color (seconds) Dry wipe with alkaline phosphatase (1 unit/mL) | Time to develop color (seconds) Wet wipe with alkaline phosphatase (3.5 units/mL) |
|---|---|---|---|
| 1 | None (Untreated) | 540 | 600 |
| 2 | None (Untreated) | 480 | 600 |
| 3 | (N-trimethoxysilylpropyl)polyethyleneimine | 35 | NA[1] |
| 4 | (N-trimethoxysilylpropyl)polyethyleneimine | 30 | 50 |
| 5 | N-trimethoxysilylpropyl-N,N,N-trimethylammonium chloride | 35 | 60 |
| 6 | N-trimethoxysilylpropyl-N,N,N-trimethylammonium chloride | 25 | 60 |

[1]Response time was not recorded.

Example 31

A blood detection pad was removed from a Multistix™ Reagent Strip for urinalysis (commercially available from Bayer HealthCare LLC, Diagnostics Division, of Tarrytown, N.Y.). The blood detection pad was dipped into tap water and allowed to soak for 1, 3, and 5 minutes. Subsequently, the pad was dipped into a 1:10,000 dilution of defibrinated sheep's blood (commercially available from PML Microbiologicals of Wilsonville, Oreg., catalog #A0408). The results below indicate that the blood detection pad was able to detect dilute blood even when pre-soaked in water for 5 minutes. Results are shown in Table 23.

TABLE 23

| Tap water soak time (minutes) | Color of blood detection pad after water soak | Time required for color change (seconds) | Color of blood detection pad after exposure to diluted blood |
|---|---|---|---|
| 0 | Dark Yellow | 2 | Dark Blue |
| 1 | Light Yellow | 31 | Dark Blue. |

TABLE 23-continued

| Tap water soak time (minutes) | Color of blood detection pad after water soak | Time required for color change (seconds) | Color of blood detection pad after exposure to diluted blood |
|---|---|---|---|
| 3 | Light Yellow | 15 | Blue |
| 5 | Light Yellowish Green | 90 | Dark green |

After the diluted blood detection experiment (above) was conducted, the dark green (reacted) pad was placed into water again. The green color due to blood detection did not decreased noticeably in intensity during the 72 hours during which the experiment was Example 32

All of the detection pads from a Multistix™ Reagent Strip for urinalysis (commercially available from Bayer Health-Care LLC, Diagnostics Division, of Tarrytown, N.Y.) were removed except for the blood detection pad. Detection limit for the blood detection pad is 0.015 mg hemoglobin/deciliter urine. 3M Scotch tape, (¾ inch wide satin; commercially available from 3M, St. Paul, Minn.) was placed over the detection pad and an approximately 0.5 mm hole was punched in the tape using an "Exacto" type hobby knife, in such a manner that liquid could pass through the hole in the tape and contact the detection pad. The indicator pad was placed into tap water for 10 minutes, after which time the pad appeared yellow. Then the pad was placed into 1:10,000 sheep's blood. After 25 seconds, a dark green spot was visible at the point on the detection pad where a hole had been placed in the overlying tape.

What is claimed is:

1. A biological soil detector, comprising:
A solid support member;
A specific indicator immobilized on the solid support member, the specific indicator comprising a material sensitive to the presence of blood;
The solid support and specific indicator positioned with respect to the detector to facilitate contact with a liquid that has been used to contact a surface; and
A retaining member supporting the solid support member and the specific indicator, the retaining member positioned to facilitate contact between the liquid and the solid support member, wherein the retaining member comprises a structure which channels the liquid therethrough, the solid support and specific indicator positioned within or on the retaining member to facilitate contact between the liquid and the solid support member when the liquid is channeled through the retaining member; and wherein the retaining member is a tubular member having a fluid inlet through which the liquid enters the retaining member and a fluid outlet through which the liquid exits the retaining member.

2. The biological soil detector of claim 1 wherein the solid support member comprises a first material selected from the group consisting of at least one polymer; inorganic material; and mixed organic and inorganic material.

3. The biological soil detector of claim 2 wherein the at least one polymer contains functional groups, the functional groups selected from the group consisting of carboxyl and salts thereof, aldehydes, sulfonic acid and salts thereof, phosphonic acid and salts thereof, alcohol, primary amine, secondary amine, tertiary amine, amide, imide, quaternized ammonium, sulfonium, phosphonium, pyridine, cyclic amido, oxyalkylene, imidazoles and combinations of two or more of the foregoing.

4. The biological soil detector of claim 3 wherein the at least one polymer containing functional groups comprises polymers and copolymers selected from the group consisting of carboxyl containing polymers; polyalkoxylates; poly (meth)acrylates; polyvinyl alcohol; polyethylene-vinyl alcohol copolymer; polyurethane; polyurea; polyester; polyamide; polyimide; polyether; cellulose; rayon; polyphosphate; polypeptide; polyacrylonitrile; polyacrylamide; polycarbonate; polyethersulfone; and combinations of two or more of the foregoing.

5. The biological soil detector of claim 2 wherein the inorganic material is selected from the group consisting of metal oxide, metal hydrate, metal-hydroxyl and combinations of two or more of the foregoing, and wherein the metal is Si.

6. The biological soil detector of claim 2 wherein the mixed organic and inorganic material is selected from the group consisting of polymeric composites, ceramers, and combinations thereof.

7. The biological soil detector of claim 1 wherein the solid support member comprises a first material selected from the group consisting of at least one polymer, inorganic material, and mixed organic and inorganic material; and a second material attached to the first material.

8. The biological soil detector of claim 7 wherein the first material is selected from the group consisting of polypropylene, polyethylene, polyvinylidene fluoride, tetrafluoroethylene hexafluoropropylene vinylidene fluoride, polyurethane, polyurea, polyester, polyvinyl acetate, polyamide, polyimide, poly(meth)acrylate, polyethersulfone, glass, silica, cellulosics, rayon, polycarbonate, polyvinyl alcohol, polystyrene, and combinations of the foregoing.

9. The biological soil detector of claim 8 wherein the second material is hydrophilic and is selected from the group consisting of monomer, polymer, reactive metal alkoxide and combinations of two or more of the foregoing.

10. The biological soil detector of claim 9 wherein the second material comprises one or more functional groups selected from the group consisting of carboxyl and salts thereof, aldehyde, sulfonic acid and salts thereof, phosphonic acid and salts thereof, alcohol, primary amine, secondary amine, tertiary amine, amide, imide, quaternized ammonium, sulfonium, phosphonium, pyridine, cyclic amido, oxyalkylene, ω-saccharinamidoundecylsiloxane, glycidyl, succinimido, imidazoles and combinations of two or more of the foregoing.

11. The biological soil detector of claim 2 wherein the solid support member comprises a material selected from the group consisting of films, nonwoven material, woven material, knitted material, reticulated foam, open-celled foam, porous ceramic inorganic frit, fiber, particle-coated supports, sintered particles, sintered fiber, sponge, and polymer membrane.

12. The biological soil detector of claim 11 wherein the polymer membrane comprises a thermally induced phase separation membrane comprising, a material selected from the group consisting of high density polyethylene, polypropylene, polyvinylidenefluoride, polyethylene-vinyl copolymer and combinations of two or more of the foregoing.

13. The biological soil detector of claim 2 wherein the solid support member further comprises a hydrophilic coating.

14. The biological soil detector of claim 1 wherein the specific indicator comprises a material sensitive to one or more blood proteins.

15. The biological soil detector of claim 1 wherein the specific indicator comprises one or more compounds which react with the product of peroxide and heme.

16. The biological soil detector of claim 1 wherein the specific indicator comprises 3,3',5,5'-tetramethylbenzidine.

17. The biological soil detector of claim 1, wherein the solid support and specific indicator are positioned within the retaining member between the fluid inlet and the fluid outlet.

18. The biological soil detector of claim 17 wherein the solid support and specific indicator are releasably positioned within the retaining member.

19. The biological soil detector of claim 17 further comprising a flow indicator, the flow indicator presenting a first appearance when the flow indicator is dry and a second appearance when the flow indicator has been exposed to the liquid.

20. The biological soil detector of claim 19 wherein the flow indicator is positioned near the specific indicator so that the second appearance of the flow indicator is an indication that the specific indicator has been exposed to the liquid.

21. The biological soil detector of claim 1 wherein the solid support and specific indicator are positioned on the retaining member to facilitate contact between the liquid and the solid support member when the liquid is channeled through the retaining member.

22. The biological soil detector of claim 21 wherein the solid support and specific indicator are positioned near the fluid inlet.

23. The biological soil detector of claim 17, wherein the solid support and specific indicator are releasably positioned near the fluid outlet.

24. The biological soil detector of claim 22 further comprising a flow indicator, the flow indicator presenting a first appearance when the flow indicator is dry and a second appearance when the flow indicator has been exposed to the liquid.

25. The biological soil detector of claim 24 wherein the flow indicator is positioned near the specific indicator so that the second appearance of the flow indicator is an indication that the specific indicator has been exposed to the liquid.

* * * * *

UNITED STATES PATENT AND TRADEMARK OFFICE
CERTIFICATE OF CORRECTION

PATENT NO. : 7,468,272 B2
APPLICATION NO. : 10/967394
DATED : December 23, 2008
INVENTOR(S) : Sailaja Chandrapati It is certified that error appears in the above-identified patent and that said Letters Patent is hereby corrected as shown below:

Title Page 2, Column 1 (Foreign Patent Documents) item 56
Line 9, Delete "2/2002" and insert -- 2/2000 --, therefor.

Column 14
Lines 22, 51, 62 and 65, Delete "calorimetric" and insert -- colorimetric --, therefor.

Column 15
Line 36, Delete "calorimetric" and insert -- colorimetric --, therefor.

Column 18
Lines 13 and 31, Delete "calorimetric" and insert -- colorimetric --, therefor.

Column 19
Line 12, Delete "calorimetric" and insert -- colorimetric --, therefor.

Column 29
Line 53, Before "solution" insert -- of --.

Column 34
Lines 1 and 54, Delete "calorimetric" and insert -- colorimetric --, therefor.
Line 56, Delete "regent" and insert -- reagent --, therefor.

Column 35
Line 21, Before "SAMCO" insert -- ( --.
Line 28, Delete "calorimetric" and insert -- colorimetric --, therefor.
Line 36, Delete "and" and insert -- any --, therefor.
Line 67, Delete "sigma" and insert -- Sigma --, therefor.

Column 36
Line 38, Delete "calorimetric" and insert -- colorimetric --, therefor.

Column 37
Line 16, Delete "calorimetric" and insert -- colorimetric --, therefor.

Column 38
Line 24, Before "80" delete "T".
Lines 39-40, After "tested" delete "as then tested".

UNITED STATES PATENT AND TRADEMARK OFFICE
CERTIFICATE OF CORRECTION

PATENT NO. : 7,468,272 B2
APPLICATION NO. : 10/967394
DATED : December 23, 2008
INVENTOR(S) : Sailaja Chandrapati It is certified that error appears in the above-identified patent and that said Letters Patent is hereby corrected as shown below:

Column 39
Line 45, After "dissolved" insert -- in --.

Column 41
Line 36, Delete "calorimetric" and insert -- colorimetric --, therefor.
Line 39, After "358" insert -- 35.8 --.

Column 42
Line 23, Delete "ratio May 5, 1990" and insert -- ratio 5/5/90 --, therefor.
Line 40, Delete "µL" and insert -- mL --, therefor.

Column 45
Line 43, Delete "inches" and insert -- inch --, therefor.

Column 47
Line 14, Delete "decreased" and insert -- decrease --, therefor.
Line 15, After "was" insert -- conducted. --.

Signed and Sealed this

Thirteenth Day of October, 2009

David J. Kappos
*Director of the United States Patent and Trademark Office*